US009554915B2

(12) United States Patent
McCormick et al.

(10) Patent No.: US 9,554,915 B2
(45) Date of Patent: *Jan. 31, 2017

(54) DEVICE AND METHOD FOR FIXATION FOR BONE OR SOFT TISSUE DEFORMITY OF DIGITS

(71) Applicant: Wright Medical Technology, Inc., Memphis, TN (US)

(72) Inventors: Daniel F. McCormick, Memphis, TN (US); Vinay Patel, Memphis, TN (US); Scott A. Armacost, Germantown, TN (US); Timothy M. O'Kane, Munford, TN (US); Wesley Reed, Libertyville, IL (US)

(73) Assignee: Wright Medical Technology, Inc., Memphis, TN (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/494,195

(22) Filed: Sep. 23, 2014

(65) Prior Publication Data

US 2015/0011998 A1 Jan. 8, 2015

Related U.S. Application Data

(63) Continuation of application No. 13/828,593, filed on Mar. 14, 2013, now Pat. No. 9,056,014.

(Continued)

(51) Int. Cl.
*A61F 2/28* (2006.01)
*A61F 2/42* (2006.01)
(Continued)

(52) U.S. Cl.
CPC ............. *A61F 2/4225* (2013.01); *A61B 17/66* (2013.01); *A61B 17/7233* (2013.01);
(Continued)

(58) Field of Classification Search
CPC ........ A61F 2/28; A61F 2/4241; A61F 2/4225; A61F 2/442
See application file for complete search history.

(56) References Cited

U.S. PATENT DOCUMENTS 2,783,758 A 3/1957 Trott
3,872,861 A 3/1975 Tamny et al.
(Continued)

FOREIGN PATENT DOCUMENTS

CN 85106151 A 11/1986
CN 201602925 U 10/2010
(Continued)

OTHER PUBLICATIONS

European Search Report for Application No. EP 13198279.5 dated May 2, 2014.
(Continued)

*Primary Examiner* — Jason-Dennis Stewart
(74) *Attorney, Agent, or Firm* — Duane Morris LLP

(57) ABSTRACT

A fixation device comprises a first clamping member having an adjustable clamping collar and a first curved support portion attached to the adjustable clamping collar. The first clamping member is adapted to receive a digit. The first curved support portion is adapted to support an inferior surface of a proximal phalanx of the digit. A distal member is adjustably attachable to the first clamping member. The distal member has a second curved support surface adapted to support an inferior surface of a distal phalanx of the digit and a curved distal end adapted to apply a compressive force in a proximal direction to a distal end of the distal phalanx.

11 Claims, 23 Drawing Sheets

Related U.S. Application Data

(60) Provisional application No. 61/746,426, filed on Dec. 27, 2012.

(51) Int. Cl.
| | | |
|---|---|---|
| *A61F 5/01* | (2006.01) | |
| *A61F 5/10* | (2006.01) | |
| *A61B 17/72* | (2006.01) | |
| *A61B 17/66* | (2006.01) | |
| *A61F 5/058* | (2006.01) | |
| *A61B 17/86* | (2006.01) | |
| *A61B 17/60* | (2006.01) | |

(52) U.S. Cl.
CPC .......... *A61B 17/7291* (2013.01); *A61F 5/019* (2013.01); *A61F 5/10* (2013.01); *A61B 17/86* (2013.01); *A61B 2017/606* (2013.01); *A61F 5/05875* (2013.01)

(56) References Cited

U.S. PATENT DOCUMENTS

| | | |
|---|---|---|
| 4,644,941 A | 2/1987 | Ogle, II |
| 5,649,541 A | 7/1997 | Stuckey |
| 5,947,915 A | 9/1999 | Thibodo, Jr. |
| 6,575,925 B1 | 6/2003 | Noble |
| 2008/0255487 A1 | 10/2008 | Bolla |
| 2011/0125265 A1 | 5/2011 | Bagga et al. |
| 2011/0301652 A1 | 12/2011 | Reed et al. |

FOREIGN PATENT DOCUMENTS

| | | |
|---|---|---|
| CN | 202397658 U | 8/2012 |
| JP | S61-011039 A | 1/1986 |

OTHER PUBLICATIONS

Office Action issued on Mar. 4, 2016, for corresponding Chinese patent application No. 201310740887.3, 5 pages.

DEVICE AND METHOD FOR FIXATION FOR BONE OR SOFT TISSUE DEFORMITY OF DIGITS

CROSS-REFERENCE TO RELATED APPLICATIONS

This application is a continuation of U.S. patent application Ser. No. 13/828,593, filed Mar. 14, 2013, which claims the benefit of U.S. provisional application No. 61/746,426, filed on Dec. 27, 2012, the entireties of which is incorporated herein by reference.

FIELD

This disclosure relates to medical devices.

BACKGROUND

Fingers and toes may become deformed. A hammertoe is a deformity of the tissues surrounding the bony structures of the lesser toes. The patient's toes elevate and cause discomfort while wearing shoes. For example, poorly fitting shoes can cause a hammertoe deformity of the proximal interphalangeal (PIP) joint of any of the lesser toes causing it to be permanently bent. Osteoarthritis, rheumatoid arthritis, stroke, Charcot-Marie-Tooth disease or diabetes may cause muscle, nerve, or joint damage which may also deform one or more joints.

Depending on the degree of deformity and the patient's history, a doctor may determine that fixation of the affected digit is appropriate to correct the deformity. For example, Wright Medical Technologies of Arlington, Tenn. provides the "PRO-TOE"® line of bone implants for correcting a hammertoe deformity. A threaded member has a longitudinal axis and threads extending from the proximal end to the distal end. A toothed blade is integrally attached to the distal end of the threaded member. The blade extends in a radial direction away from the longitudinal axis. The blade has an outer edge with a plurality of teeth on it.

Improved fixation devices and methods are desired for correcting joint deformities, such as hammertoe and the like.

SUMMARY

In some embodiments, a fixation device comprises a first clamping member having an adjustable clamping collar and a first curved support portion attached to the adjustable clamping collar. The first clamping member is adapted to receive a digit therethrough. The first curved support portion is adapted to support an inferior surface of a proximal phalanx of the digit. A distal member is adjustably attachable to the first clamping member. The distal member has a second curved support surface adapted to support an inferior surface of a distal phalanx of the digit and a curved distal end adapted to apply a compressive force in a proximal direction to a distal end of the distal phalanx.

In some embodiments, a fixation device comprises a proximal clamping member and a distal clamping member. Each of the proximal and distal clamping members has an adjustable clamping collar adapted to receive a digit therethrough. First and second coaxial helical members are provided, opposing each other. Each of the helical members has a respective proximal end fixedly attached to the proximal clamping member and a respective distal end fixedly attached to the distal clamping member.

In some embodiments, a fixation device comprises a proximal clamping member and a distal clamping member. Each of the proximal and distal clamping members has an adjustable clamping collar adapted to receive a digit therethrough. A plurality of longitudinal spacers each have a proximal end attached to the proximal clamping member and a distal end attached to the distal clamping member. A plurality of spring members have a proximal end attached to the proximal clamping member and a distal end attached to the distal clamping member. Each spring member is located adjacent to and radially inward from a respective longitudinal spacer. Each longitudinal spacer constrains its respective spring member to bow radially inwards.

In some embodiments, a fixation device comprises a tube comprising a contractible tubular woven mesh configured to contract radially under longitudinal tension. At least one helical yarn or fiber is fastened at or near a first end of the tube and woven helically through the mesh and extends from a second end of the tube opposite the first end of the tube, such that the yarn is capable of applying radial compression to the tube when placed under tension.

In some embodiments, a fixation device comprises a tube comprising a contractible tubular woven mesh configured to contract radially under longitudinal tension. A plurality of sleeves are arranged around an outer surface of the tube, the sleeves smaller in diameter than the tube. At least one rib is removably insertable in at least a respective one of the plurality of sleeves. The at least one rib is formed of a material that is more rigid than a material of the tubular woven mesh.

In some embodiments, a bone implant comprises a helical threaded member having first and second ends and a longitudinal central opening extending from the first end to the second end. The longitudinal central opening has a longitudinal axis. At least one blade is integrally attached to the first end of the helical threaded member. The blade extends in a radial direction away from the longitudinal axis. The blade has an outer edge with a plurality of teeth thereon.

In some embodiments, a bone implant comprises a central shaft having first and second ends and a longitudinal axis. A first set of blades are integrally attached to the first end of the central shaft. The first set of blades extend in a radial direction away from the central shaft. Each of the first set of blades having an outer edge with a plurality of teeth thereon. A second set of blades are integrally attached to the second end of the central shaft. The second set of blades extend in the radial direction away from the central shaft. Each of the second set of blades has an outer edge with a plurality of teeth thereon. The second set of blades are rotationally offset from the first set of blades.

DETAILED DESCRIPTION

Figure 1:
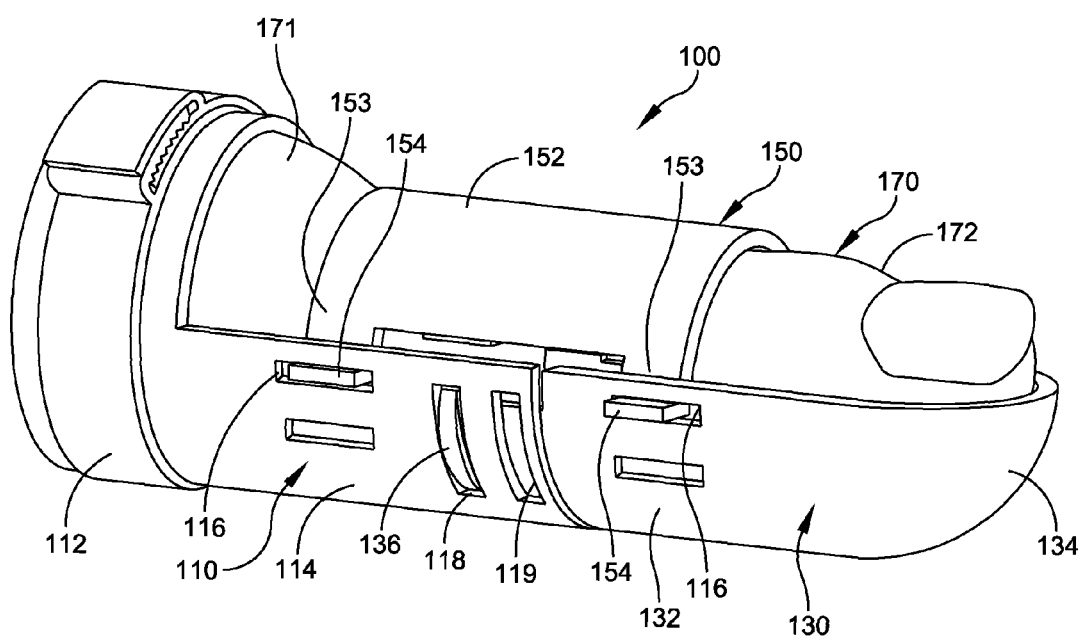
FIG. 1 is a side perspective view of an external fixation/correction device formed in accordance with an embodiment of the invention for use in correcting deformities in a toe or finger.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 2:
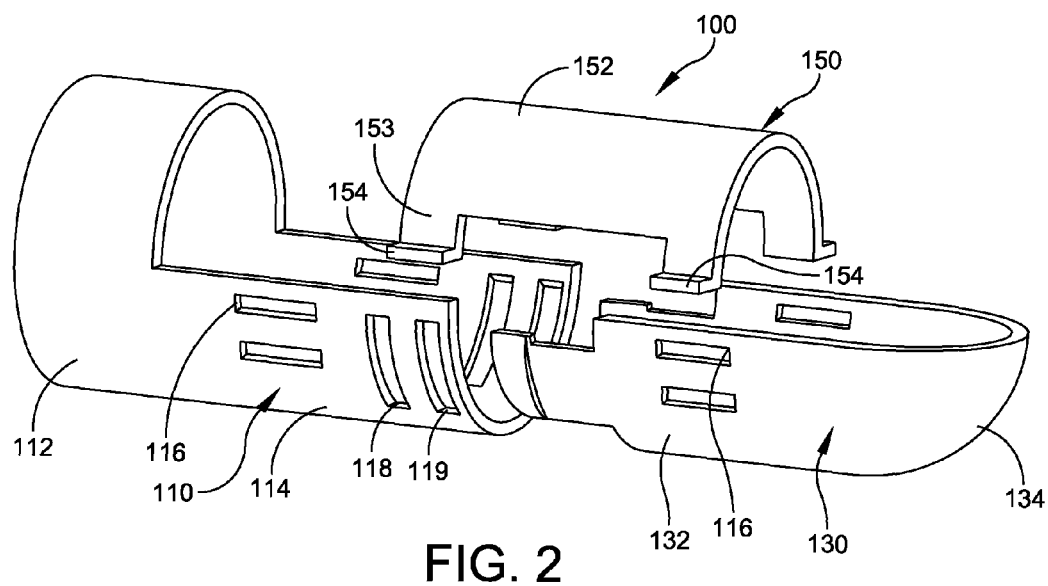
FIG. 2 is a perspective exploded view of the external fixation/correction device shown in FIG. 1.
Figure 3:
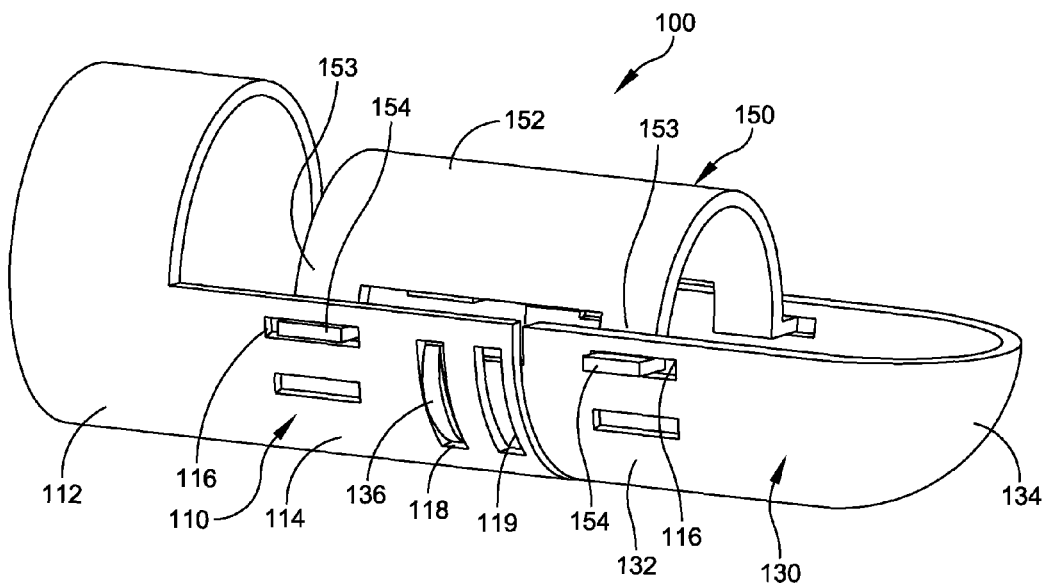
FIG. 3 is a perspective view of the external fixation/correction device shown in FIGS. 1 and 2 with a superior member engage with remainder of the device.

FIGS. 1 to 3 show an embodiment of an external fixation device 100. FIG. 2 is an exploded view. FIG. 3 shows the assembled device. Once assembled and applied to a digit (e.g., toe), the device 100 achieves axial compression, radial compression and superior/inferior stabilization. The device 100 can be used by itself for non-invasive treatment, or as a fixation and support device during recovery from a surgical procedure. FIG. 1 shows the assembled device in use for correcting a hammertoe deformity.

The device 100 has a proximal first clamping member 110 having an adjustable clamping collar 112 and a first curved support portion 114 attached to the adjustable clamping collar 112. The first clamping member 110 is adapted to receive a digit 170 (e.g., a toe or finger) therethrough. The first curved support portion 114 is adapted to support an inferior surface of a proximal phalanx 171 of the digit 170. The circular clamping collar 112 allows for radial compression on the proximal side of the joint-line. The collar 112 as shown has a ratchet mechanism with ramped teeth which permit tightening, but retain the clamp in position once tightened.

Although FIG. 1 shows ratchet type clamping collar 112, other clamping collars can be used. For example, some embodiments include a clamping mechanism of a type used in cable ties. Some embodiments include a hook and locking latch type clamping collar. Some embodiments include a worm drive clamping mechanism (similar to the drive of a hose clamp). Other embodiments include circular springs of various configurations, which the doctor can pinch to expand, and which are biased to contract and provide compression upon release. Other embodiments include hook and loop fasteners on ends of a band encircling the clamping collar 112. These are only examples of clamping mechanisms, and other embodiments include other types of clamping mechanisms.

A distal member 130 is adjustably attachable to the first clamping member 110. The distal member 130 has a second curved support surface 132 adapted to support the inferior surface of a distal phalanx of the digit 170 and a curved distal end 134 adapted to apply a compressive force in a proximal direction to a distal end of the distal phalanx 172.

In some embodiments, the distal member 130 has a hemispherical distal surface which is sized and shaped to receive the most distal end of a digit (toe or finger). In some embodiments, the superior member has cantilever arms 153, each having a locking tab 154 adapted to mate with the respective slot 116 of the clamping member 110.

An superior member 150 is configured to be attached to the first clamping member 110 and the distal member 130. The superior member 150 has a curved surface 152 adapted to apply a force against a superior surface of the digit 170. When the joint is flexed, the superior member 150 assists in correcting that flex. In some embodiments, the superior member 150 has spring-like material properties, a circular profile, and tabs 154, which interlock with slots 116 in both the clamping member 110 and distal member 130. Some embodiments include a plurality of locking tabs 154 or a plurality of slots 116 inferiorly, to allow incremental increase of compression. Each respective slot 116 is configured to receive the at least one tab 154 with the superior member 150 at a respectively different location relative to the proximal member 110 & distal member 130, for applying a respectively different compressive force in the inferior direction. For example, in the embodiment of FIG. 1, clamping member 110 has two slots 116, and superior member 150 has tab 154.

The superior member has means for locking the superior member to the first clamping member and the distal member. In some embodiments, the superior member 150 has one of the group consisting of a slot 116 and a locking tab 154, either of which provides a locking means. At least one of the first clamping member 110 and the distal member 130 has the other of the group consisting of a slot 116 and a locking tab 154 for engaging the slot or locking tab of the superior member. For example, in the embodiment of FIG. 1, clamping member 110 and distal member 130 each have a slot 116, and superior member 150 has locking tab 154. In an alternative embodiment, the superior member 150 has slots, and the clamping member 110 and distal member 130 each have a locking tab for mating with the slots of the superior member 150. In another embodiment, the superior member has a slot at one end and tab at the other end; one of the clamping member 110 and the distal member 130 has a tab and the other has a slot, for mating with the respective slot and tab of the superior member 150.

In some embodiments, the clamping member 110, distal member 130 and superior member 150 are made of padded stainless or titanium alloy.

In some embodiments, one of the first clamping member 110 and the distal member 130 includes at least one locking tab 136, and the other of the first clamping member 110 and the distal member 130 includes a plurality of slots 118, 119. Each respective slot 118, 119 is configured to receive the at least one locking tab 136 with the distal member 130 at a respectively different location relative to the proximal member 110, for applying a respectively different compressive force in the proximal direction. For example, in the embodiment of FIG. 1, clamping member 110 has two slots 118 and 119, and distal member 130 has locking tab 136. In some embodiments, the locking tab 136 has ramped surface for easy insertion, and for retaining the distal member 130 in position relative to the clamping member 110, absent an affirmative user action to release the tab 136 from the slot 118 or 119.

In some embodiments, the slots 116 are substantially longer than the width of tabs 154, so that the superior member 150 can move along the longitudinal (proximal-distal) axis. This allows the selection of slot 118 or 119 to determine the engagement depth of the distal member 130 relative to the clamping member 110, for control of the compression force against the distal end 172 of the digit 170.

An exemplary method of using the device 100 is as follows:

1. The user secures the device 100 to the proximal side 171 of the joint, using the adjustable clamping collar 112 on the clamping member 110.

2. The user assembles the distal member 130 to the clamping member 110 by engaging the tabs 154 of the cantilever arms 153 into the slots 116 of the clamping member 110.

a. The engagement depth of the tabs 136 determines the amount of axial compression. Various engagement depth options are provided with multiple slots. The embodiment of FIG. 1 has two slots 118, 119, providing two engagement depth options. Other embodiments include other numbers of slots for this purpose (e.g., one, three, four or the like).

3. The user assembles the superior member 150 to the clamping member 110 and distal member 130 by compressing the tabs 154 of the superior member 150 inward and aligning the tabs 154 with the mating slots 116 of the clamping member 110 and distal member 130.

a. The amount of superior compression is determined by the mating features selected (overlapping in the superior / inferior axis by selection of one of the slots 116), the degree of semi-circularity (i.e., the angle of the sector of a cylinder that the superior member 150 subtends), as well as the material properties of the superior member 150.

Figure 4:
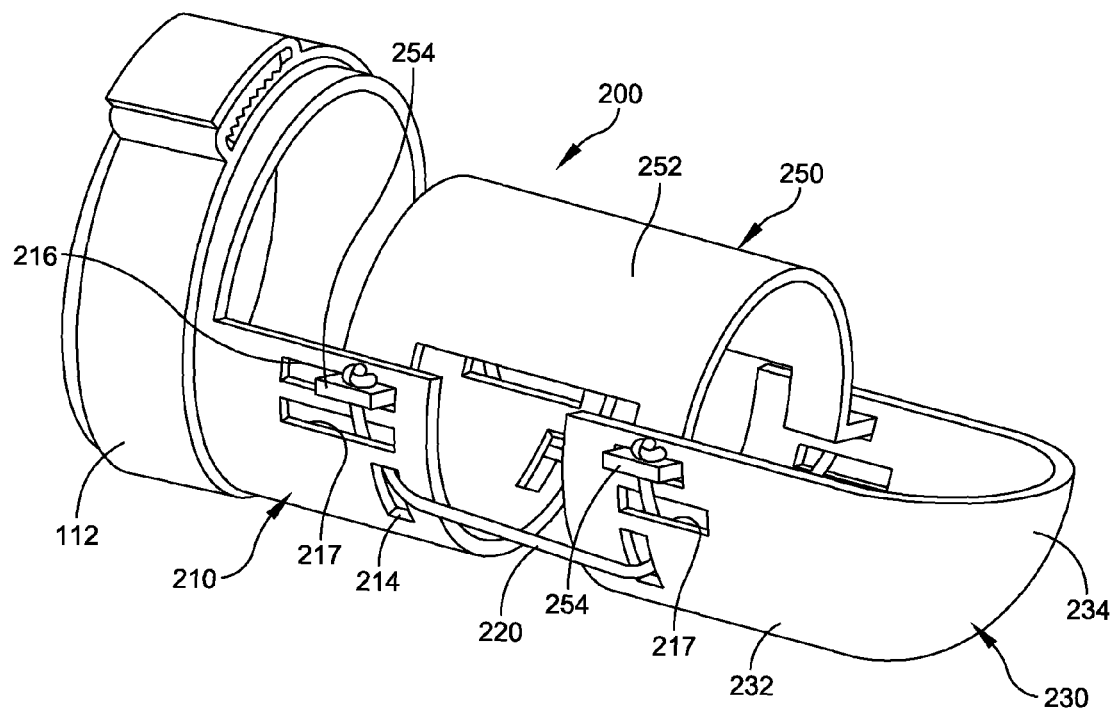
FIG. 4 is a perspective view of an alternative embodiment of external fixation/correction device including a strap or band woven through slots in the clamping member.

FIG. 4 shows another embodiment of a fixation device 200. A first clamping member 210 has an adjustable clamping collar (not shown) at its proximal end and a first curved support portion 214 attached to the adjustable clamping collar. The device 200 of FIG. 4 can include any type of clamp 112 described above with respect to the device 100 of FIGS. 1-3, and solely for brevity, descriptions thereof are not repeated. The first clamping member 210 is adapted to receive a digit (not shown). The first curved support portion 214 is adapted to support the inferior surface of a proximal phalanx of the digit. A distal member 230 is adjustably attachable to the first clamping member 210. The distal member 230 has a second curved support surface 232 adapted to support an inferior surface of a distal phalanx of the digit and a curved distal end 234 adapted to apply a compressive force in a proximal direction to a distal end of the distal phalanx. A superior member 250 is configured to be attached to the first clamping member 210 and the distal member 230. The superior member 250 has a curved surface 252 adapted to apply a force against a superior surface of the digit.

The device 200 of FIG. 4 differs from the embodiment of FIGS. 1-3 in that it has a different means for locking the superior member to the first clamping member and the distal member. Device 200 has a fully adjustable locking means including at least one suture, strap or band 220 on each side (medial and lateral) of the device 200. The at least one suture, strap or band 220 is formed of a strong, flexible material, such as nitinol or ultra-high molecular weight polyethylene (UHMWPE) suture material, or nylon. The suture, strap or band 220 is woven through the slots 216, 217 in the clamping member 210 and distal member, and attached to the tabs 254 of the superior member 250. The tabs 254 are inserted through one of the slots 216, selected to control the force applied by superior member 250.

This embodiment of the device 250 can be placed on the patient while fully assembled and then the suture, strap or band 220 tightened until the desired compression is reached. The mechanism provides a locking feature such that compression is not lost through repetitious motion.

In some embodiments, the means for locking also includes a release, or unloading, method in the event that the desired compression decreases with time.

Figure 5:
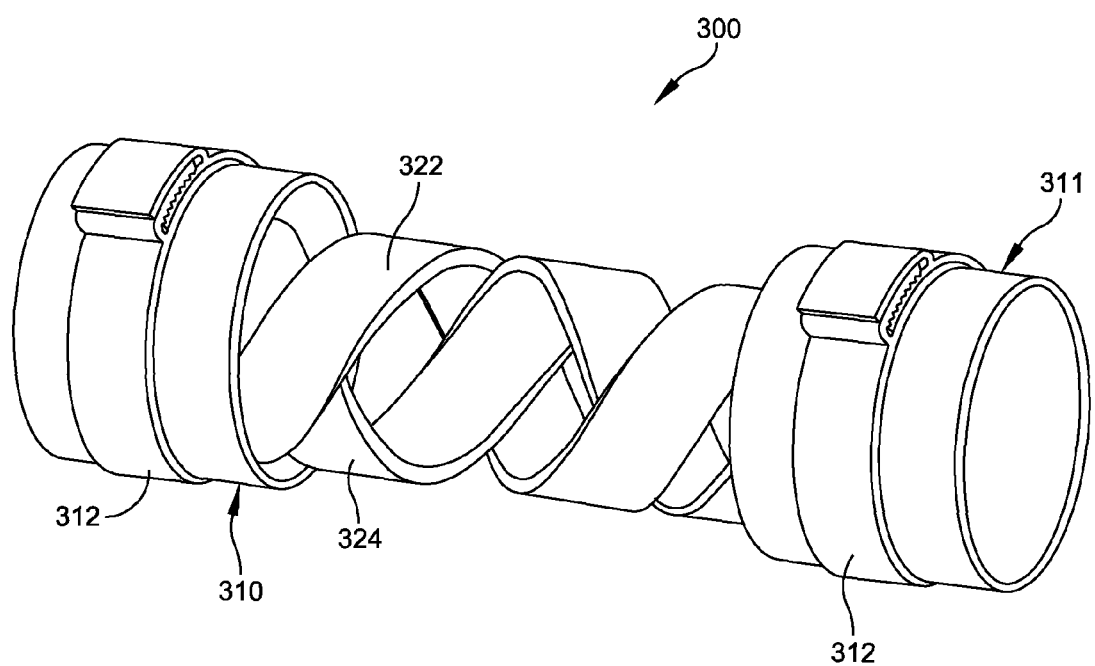
FIG. 5 is a side perspective view of a second embodiment of external fixation/correction device for use in correcting deformities of a toe or finger.
Figure 6:
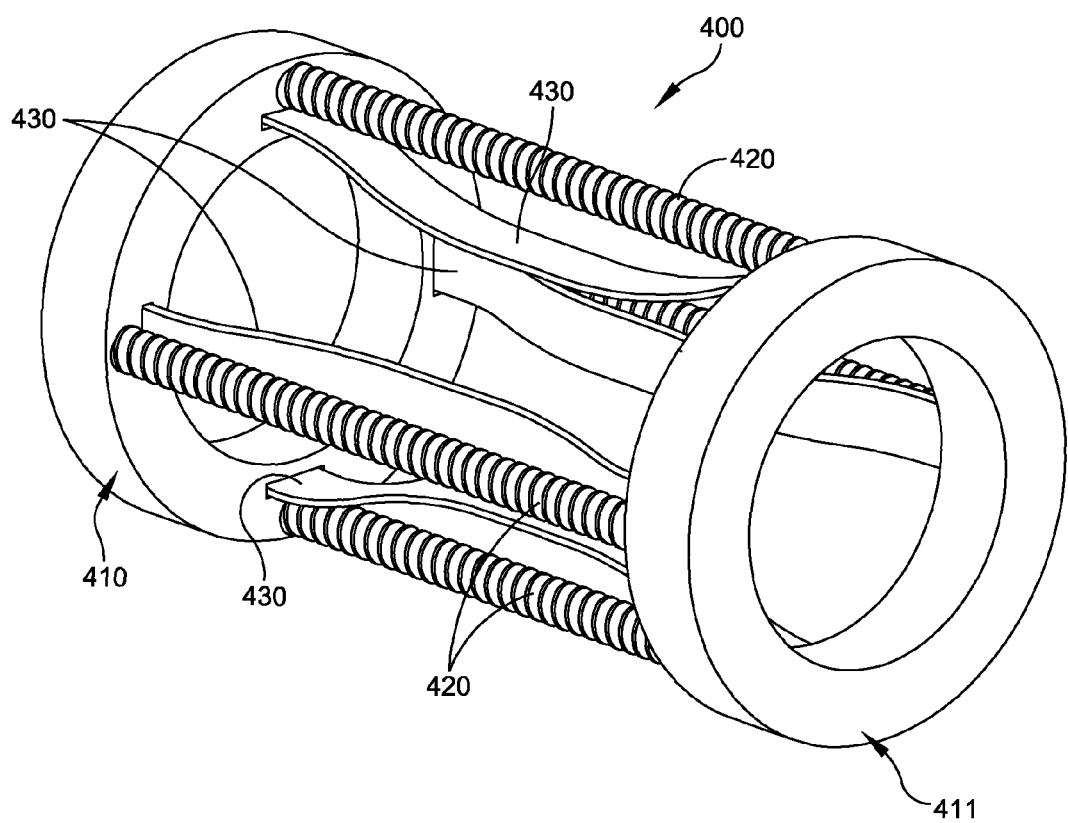
FIG. 6 is a perspective view of a third embodiment of external fixation/correction device for use in correcting deformities of the toe or finger.
Figure 7:
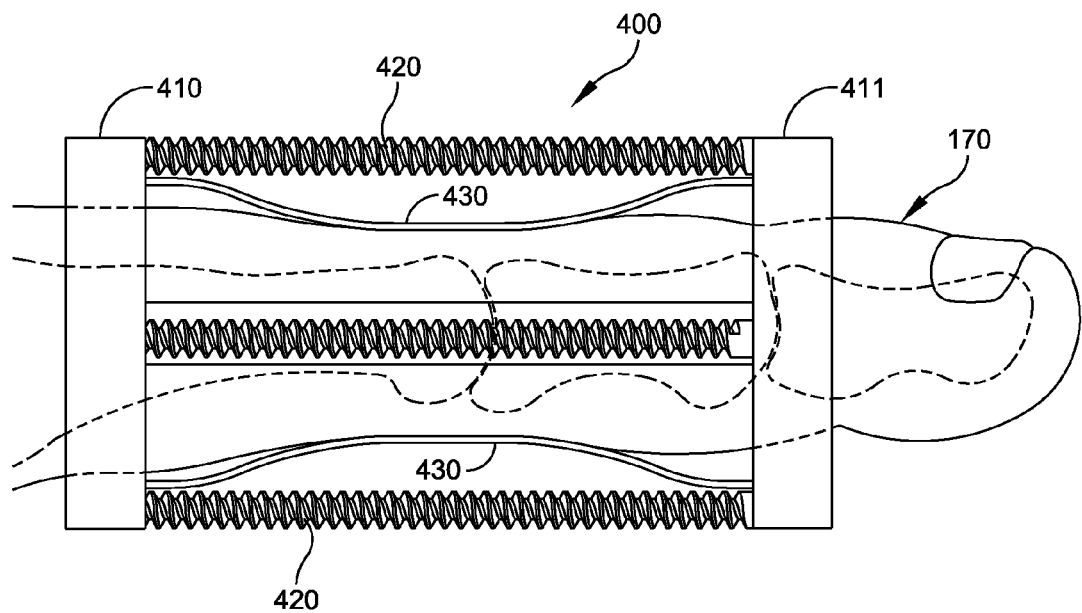
FIG. 7 is a side elevational view of the external fixation/correction device shown in FIG. 6, with a broken away, partially phantom finger positioned within the device.
Figure 8:
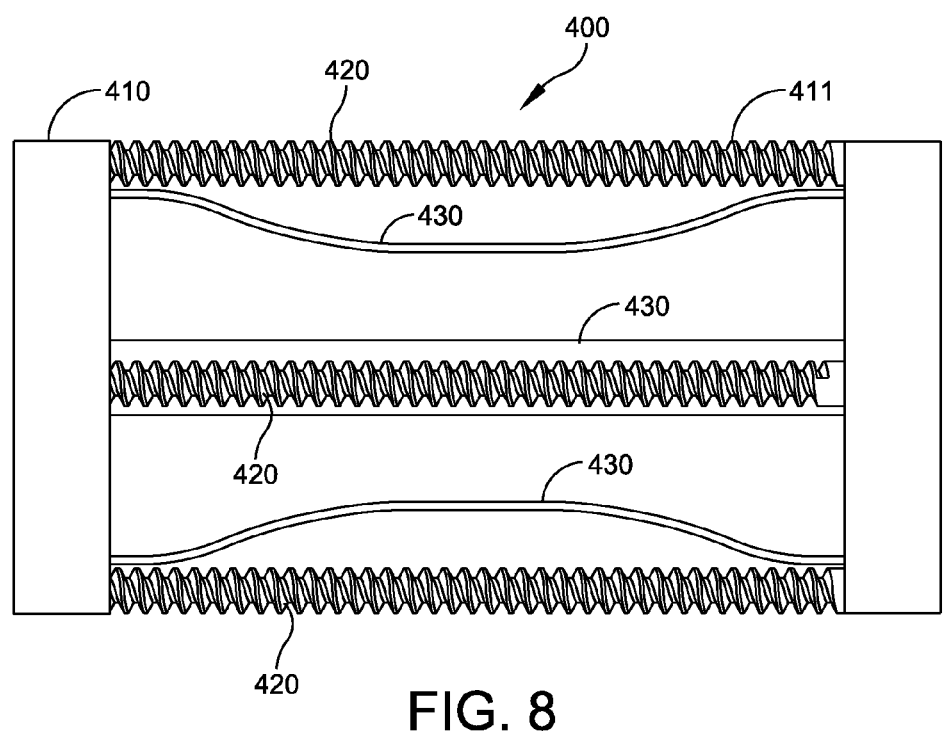
FIG. 8 is a side elevational view of the external fixation/correction device shown in FIG. 7.

Although FIG. 4 shows a suture, strap or band 220, in other embodiments other mechanisms are substituted, such as, but not limited to:

a. Cable tie configurations
b. Enhanced hook and loop fastener for increased holding strength
c. Strap/buckle mating device
d. Super-elastic ribbon/Shape set to distances that provides compression, stretched to fit over surgical site and allowed to return to its natural state providing the desired compression.
e. UHMWPE Suture with locking technology integrated in mating features FIG. 5 shows an embodiment of a fixation device 300, comprising a proximal clamping member 310 and a distal clamping member 311. Each of the proximal and distal clamping members 310, 311 has an adjustable clamping collar 112 adapted to receive a digit 170 therethrough. The device 300 of FIG. 5 can include any type of clamp 112 described above with respect to the device 100 of FIGS. 1-3, and solely for brevity, descriptions thereof are not repeated.

The device 300 has first and second coaxial helical members 322 and 324 opposing each other. For example, in FIG. 5, from left to right, helical member 322 is wound in a clockwise direction around a longitudinal axis of the device 300, and helical member 324 is wound in a counter-clockwise direction around the longitudinal axis. Each of the helical members 322, 324 has a respective proximal end fixedly attached to the proximal clamping member 310 and a respective distal end fixedly attached to the distal clamping member 311. In some embodiments, the helical members 322, 324 are joined to the clamping members 310, 311 by be laser-welded or other suitable technique. Each of the first and second coaxial helical members 322, 324 is in the form of helical band having an inner support surface arranged to be wrapped around the digit 170.

The helical members 322, 324 have spring-like material properties. Flexibility at the joint can be controlled by the stiffness in the material selection for the helical members. In some embodiments, the helical members 322, 324 comprise spring steel or nitinol.

In use, the clamping members 310, 311 are positioned on opposing ends of the joint-line at the surgical/treatment site.

1. The user positions one clamp proximally with respect to the joint line. The user secures the proximal clamp 312 of member 310 to fix the location of device 300.

2. The user extends the free clamp 312 axially in the distal direction, stretching the helical members 322, 324 beyond their relaxed lengths.

3. The user secures the distal clamp 312 of member 311 in the extended position.

Once installed, the helical members 322, 324 react similar to an extension spring as they are strained in extension between two fixed members 310, 311. This results in active compression across the joint acting concurrently with the radial compression created by the clamping action. Device 300 allows some flexion, but, selection of the diameter of the helical members 322, 324 allows the designer to limit the amount of flexion the device 300 affords.

FIGS. 6-11 show an embodiment of a fixation device 400, comprising a proximal clamping member 410 and a distal clamping member 411. Each of the proximal and distal clamping members 410, 411 has an adjustable clamping collar 112 (not shown in FIGS. 6-11) adapted to receive a digit therethrough. The device 400 of FIGS. 6-11 can include any type of clamp 112 described above with respect to the device 100 of FIGS. 1-3, and solely for brevity, descriptions thereof are not repeated.

Device 400 has a plurality of longitudinal spacers 420. Each longitudinal spacer 420 has a proximal end attached to the proximal clamping member 410 and a distal end attached to the distal clamping member 411. Each longitudinal spacer 420 has at least one threaded end, and one of the proximal and distal clamping members 410, 411 has a respective thread configured to receive the threaded end for adjusting a separation between the proximal and distal clamping members. In some embodiments, the clamping members have are countersunk to receive nuts 422 for receiving the threads of the spacers 420 (See FIGS. 9 and 10). In some embodiments, spacers 420 are threaded throughout their lengths. In other embodiments, the spacers 420 are threaded at each end, and have a smooth surface in between, configured to receive a tightening instrument (e.g., a wrench) to adjust a distance between the proximal and distal clamping members 410, 411.

Figure 9:
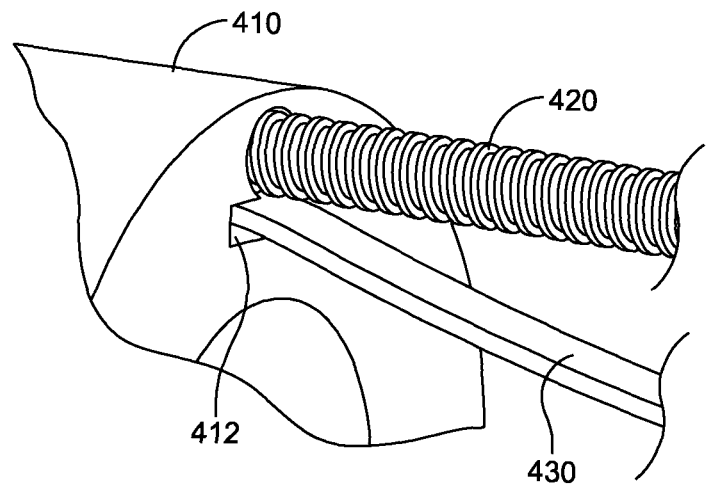
FIG. 9 is a broken away, enlarged view of a portion of the external fixation/correction device shown in FIGS. 6, 7 and 8.
Figure 10:
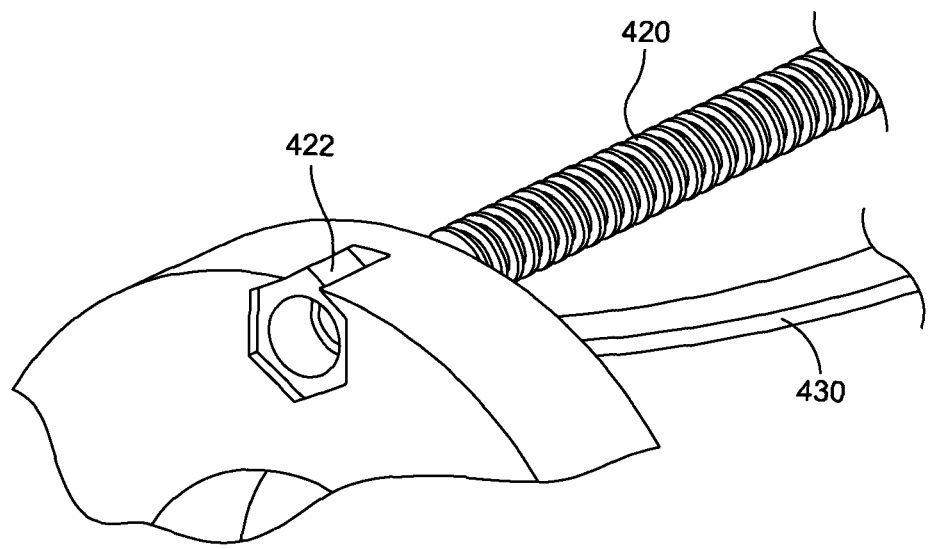
FIG. 10 is a broken away, perspective view of the external fixation/correction device shown in FIGS. 7, 8 and 9.

Device 400 has a plurality of spring members 430. Each spring member 430 has a proximal end attached to the proximal clamping member 410 and a distal end attached to the distal clamping member 411. For example, as shown in FIG. 9, each end of each spring member 430 fits in a respective slot 412 of clamping members 410 and 411. Each spring member 430 is located adjacent to and radially inward from a respective longitudinal spacer 420. Each longitudinal spacer 420 constrains its respective spring member 430 to bow radially inwards.

In the embodiment of FIGS. 6-11, the plurality of longitudinal spacers 420 includes four longitudinal spacers, and the plurality of spring members 430 include four spring members arranged approximately evenly around a circumference of the proximal clamping member and distal clamping member. Other embodiments include different numbers of spacers 420 and spring members 430 (e.g., 2 or 6).

The device 400 achieves radial compression. The adjustable clamps create a site of fixation on either side of the joint-line. Rotating the spacers 420, with their threaded ends, creates linear extension or retraction of the distance between the clamping members 410, 411.

When the spacers 420 are rotated to reduce the distance between the clamping member 410, 411, the spring members 430 bow and flex inwards as the clamping members 410, 411 translate towards each other, creating radial stability. Device 400 achieves simultaneous radial stability and axial compression at the joint-line.

Figure 11:
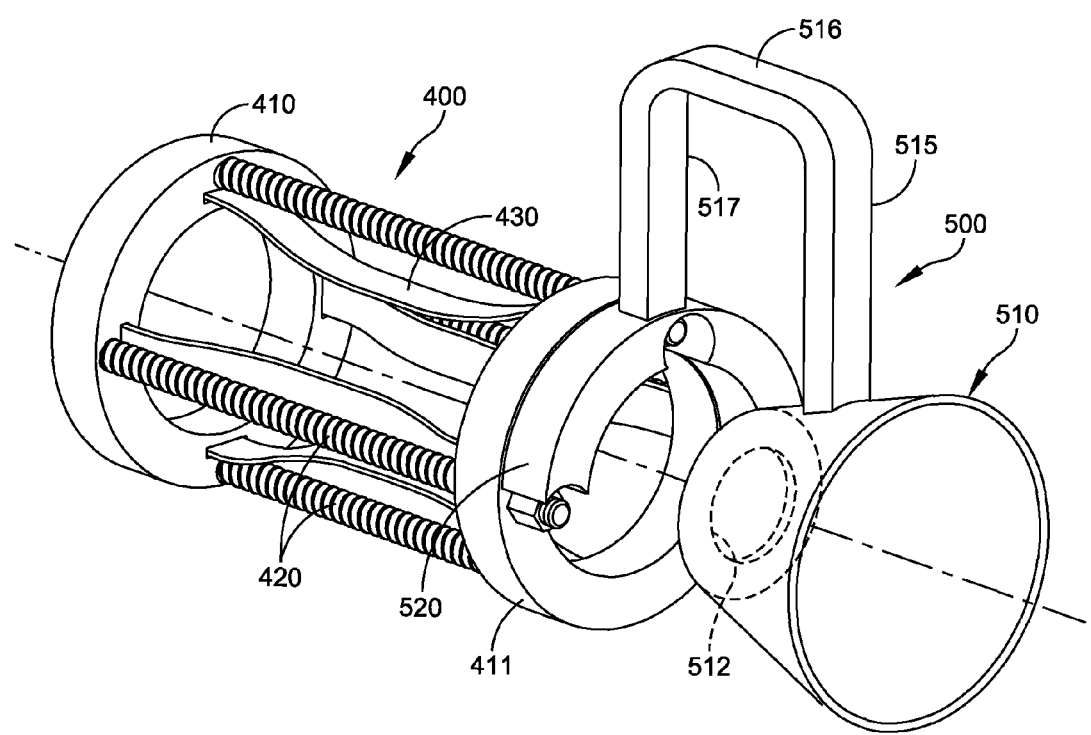
FIG. 11 is a perspective view, partially in phantom, of a drill guide suitable for use with the fixation/correction devices shown in FIGS. 1-10.

FIG. 11 shows the device 400 with a detachable drill guide 500 detachably connected to the distal clamping member 411. The detachable drill guide 500 has a guide portion 510 adapted to guide a drill along a proximal-distal axis should an intramedullary device be appropriate. The guide portion 510 has a tapered lead in guide with an opening 512, through which the drill is inserted.

The drill guide 500 comprises a support structure including at least a pair of radial arms 515, 517 and a longitudinal arm 516 for positioning the guide portion 510 a variable distance away from the distal clamping member 411. The radial arms 515, 517 and longitudinal arm 516 are extendible for varying a radial offset and a longitudinal displacement of the guide portion 510 relative to the distal clamping member 411.

Figure 11A:
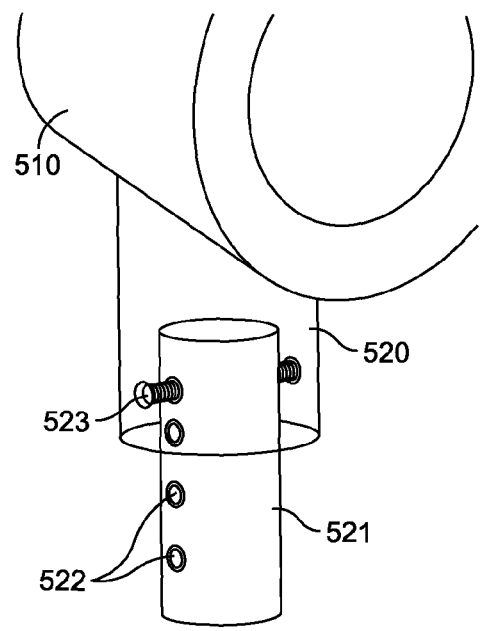
FIG. 11A is a broken away, detailed view of an adjustment mechanism for the drill guide shown in FIG. 11.
Figure 11B:
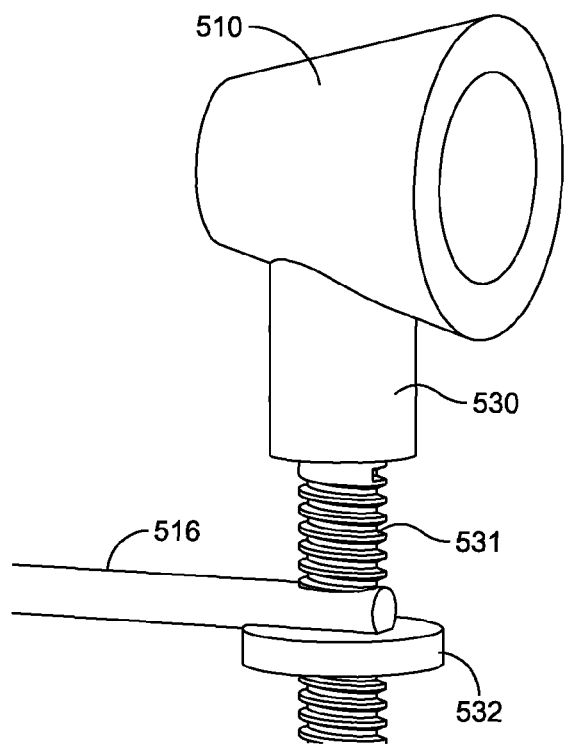
FIG. 11B is a further broken away detail of another adjustment mechanism for the drill guide shown in FIG. 11.
Figure 12:
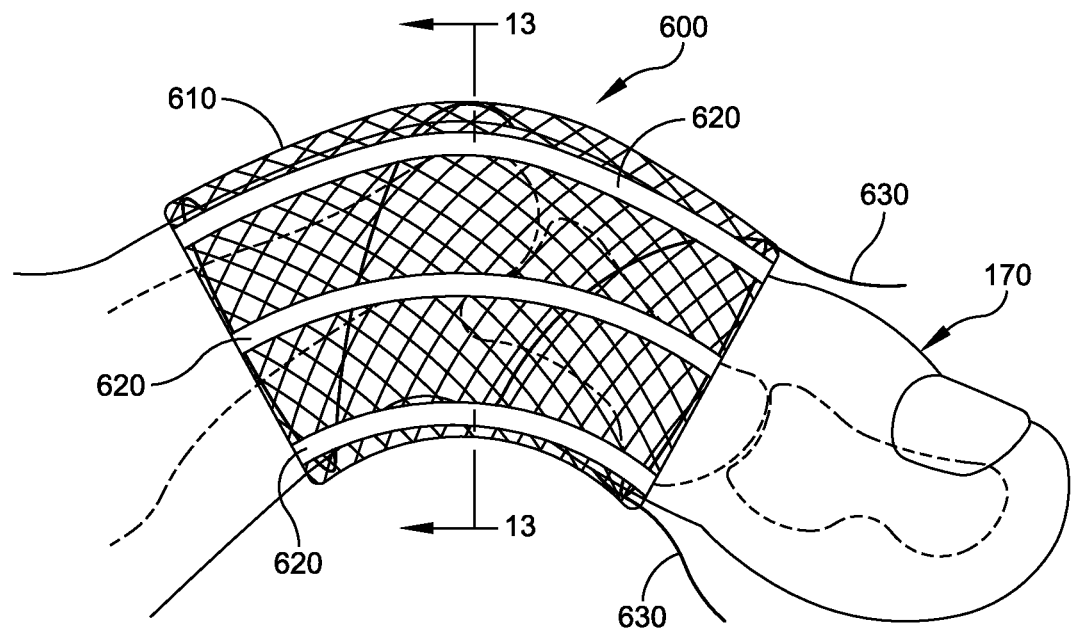
FIG. 12 is a side elevational view, partially in phantom, of yet a further embodiment of external fixation/correction device for correction of deformities in a toe or finger.
Figure 13:
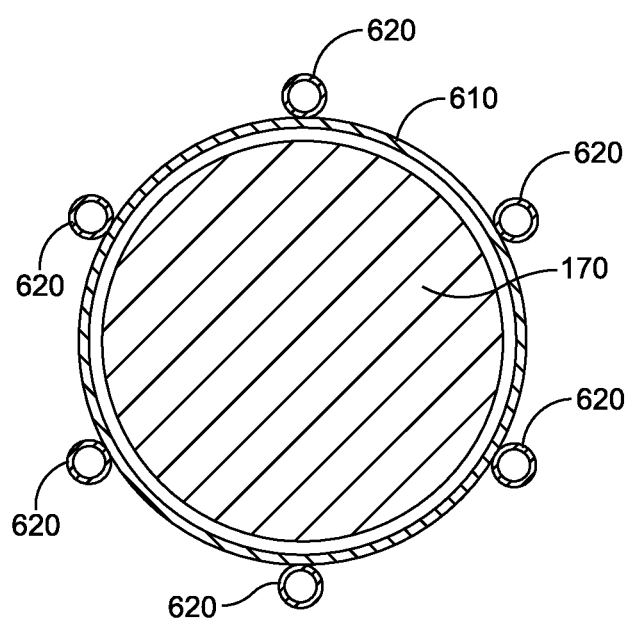
FIG. 13 is a cross sectional view taken along line 13-13 in FIG. 12.
Figure 14:
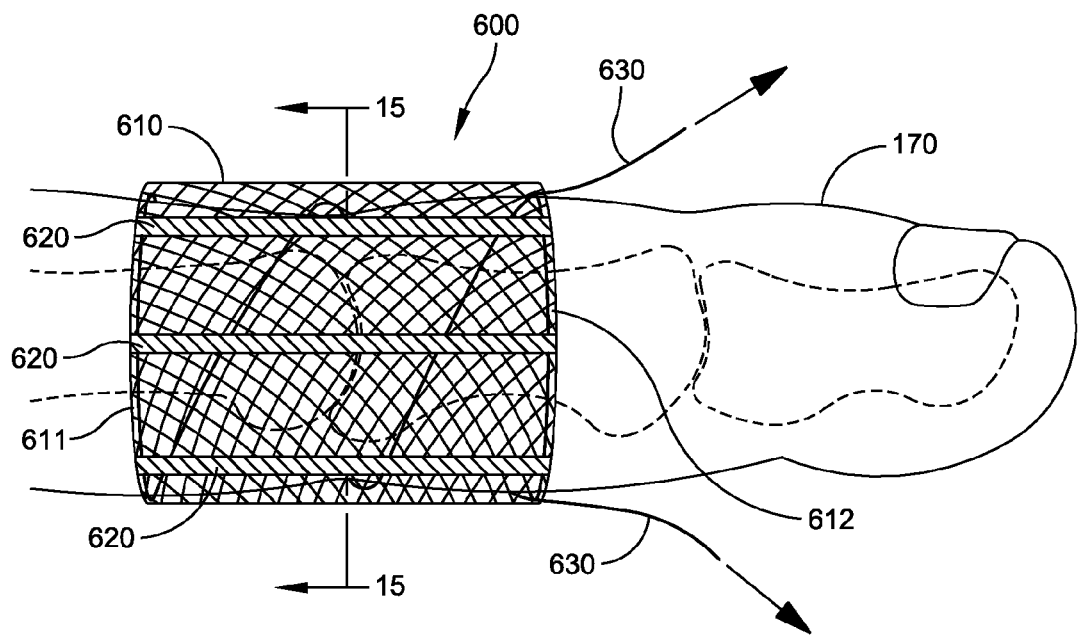
FIG. 14 is a side perspective view, partially in phantom, of the fixation/correction devices shown in FIGS. 12-13.

Some embodiments provide fine-tuning and adjustable height and length to ensure that the guide is in the desired location in both the longitudinal and superior/inferior directions. Once the desired location is determined, the adjustable arms lock into place. This achieves accurate and consistent placement of temporary fixation devices or pre-drills. Various mechanisms can be used to provide adjustability. For example, in some embodiments, as shown in FIG. 11A, the drill guide 510 and cylindrical body 520 are an assembly, wherein the cylindrical body 520 replaces the post 515 of FIG. 11. The post 521 has detents 522 at predetermined offsets from each other. The drill guide 510 has at least one spring plunger 523 threaded into the cylindrical body 520 perpendicular to the tapered guide 510. The spring plungers are biased to engage the post detents, retaining the drill guide 510 in position & will disengage upon sufficient force supplied in the direction of the post axis to allow positional adjustments of the drill guide. In another embodiment, as shown in FIG. 11B, the threaded post 531 is attached to a rod 530 & drill guide 510 as an assembly. The longitudinal post 516 is attached to a threaded nut 532 in which the nut is constrained in translation coaxially and perpendicular to the threaded axis. As the threaded nut 532 is turned, the assembly comprising the threaded post 531, rod 530 & drill guide 510 will move along the threaded body's axis per the threaded pitch. In other embodiments (not shown), the threaded post 531 mates with a worm gear attached to the post 516. As the worm gear is turned the assembly comprising the threaded post 531, rod 530 & drill guide 510 will move along the threaded body's axis per the threaded pitch.

The drill guide 500 has an attachment mechanism 520 which allows it to be secured to one of the clamping members 411. In some embodiments, the attachment mechanism is a partial collar 520 which matches a portion of the distal clamping member 411. In other embodiments (not shown), the attachment mechanism is a complete ring, matching the shape of clamping member 411.

Although the drill guide is only shown in FIG. 11, the drill guide can be used with any of the devices 100, 200, or 300 described above.

The material of drill guide 500 can be comprised of either radiopaque or radiolucent materials. A radiolucent material (e.g., hard plastic or glass filed polymer) may be desired if the assembly is to be imaged by fluoroscopy in situ, and the physician does not want the drill guide to appear in the image. A physician may desire a radiopaque material if he/she wishes to establish the position of the drill guide 500 with respect to the bone under fluoroscopy, for example.

FIGS. 12-15 show an embodiment of a fixation device 600 comprising a tube 610 comprising a contractible tubular woven mesh configured to contract radially under longitudinal tension. Such contractible tubular woven meshes are commonly referred to as "Chinese finger traps," and are described, for example, in U.S. Pat. Nos. 2,783,758, 3,872, 861 and 5,649,541, which are incorporated by reference herein.

The contractible tubular woven mesh 610 has at least one helical yarn or fiber 630 fastened at or near a first end 611 of the tube 610 and woven helically through the mesh and extending from a second end 612 of the tube 610 opposite the first end 611 of the tube, such that the yarn 630 is capable of applying radial compression to the tube when placed under tension. The helical yarn or fiber 630 is a separate yarn or fiber from those used to form the contractible tubular woven mesh 610. In some embodiments, the helix of the yarn or fiber 630 winds around the circumference of the tube 610 with a different period that the fibers which constitute the mesh of tube 610. In some embodiments, the helical yarn or fiber 630 comprises a different material from the material of the tube 610. The helical yarn or fiber provides a drawstring In some embodiments, the at least one helical yarn or fiber 630 includes two opposing yarns or fibers 630 extending in opposite directions around a circumference of the tube 610. That is, one is configured as a right hand helix and the other is a left hand helix, so that viewed in a direction of the longitudinal axis of the tube 610, one helix winds clockwise around the tube, and the other helix winds counter-clockwise around the tube. In some embodiments, the yarn or fiber 630 includes a circular winding (in a plane perpendicular to the longitudinal axis of the tube 610) at each end of the tube 610, so that pulling the string causes both radial compression and cinching of the ends of the tube 610. The helix crosses in the middle of the fixation device 600 such that when cinched, the contraction of the helical yarn or fiber 630 causes a bent joint to straighten through the application of a compressive force along the helix.

The device 600 is slipped over the digit to be treated, and the at least one helical yarn or fiber 630 is (are) pulled and tied or fastened. The at least one helical yarn or fiber 630 act as a drawstring, cinching the tube 610 and placing the tube in radial compression. In some embodiments, the device 600 is used to straighten the digit (e.g., toe) for percutaneous drilling into the end of the toe. The mesh will compress the toe while holding it rigid in line for drilling. This device 600 can also be used for minor adjustment until the soft tissue releases.

In some embodiments, the user attaches a weight to the yarns or fibers 630 to maintain compression during a surgical procedure. In other embodiments, the device 600 is used to provide stability post-surgery for a length of time by pulling, cinching and tying off the helical yarns or fibers 630. The device 600 can provide compression and help correct deformity.

In some embodiments, the device 600 is used alone to provide compression and support. In some embodiments, additional support and rigidity is provided by inclusion of optional sleeves 620. In some embodiments, a plurality of sleeves 620 are arranged around an outer surface of the tube 610. The sleeves 620 are substantially smaller in diameter than the tube 610. Any number of sleeves 620 may be included. In some embodiments, four, six or eight sleeves 620 are uniformly distributed about the circumference of the tube 610. In some embodiments, the sleeves 620 comprise the same material as the mesh of tube 610. In other embodiments, the sleeves comprise a different material from tube 610.

Each of the plurality of sleeves 620 has a respective first end fixed at or proximate to a first end 611 of the tube 610 and a respective second end fixed at or proximate to a second end 612 of the tube 610 opposite the first end 611. Each sleeve 620 has a portion that is freely movable relative to the tube 610, the portion being between the first end and second end of each sleeve. In some embodiments, the sleeves are only fixed (e.g., by sewing) at their ends to the respective ends 611, 612 of the tube 610, and the sleeves are free to move relative to the tube at all intermediate locations along the lengths of the sleeves. In other embodiments, the sleeves 620 are fixed at both ends and at one or more intermediate points along their length to the outer surface of the tube 610. In other embodiments, the sleeves 620 are sewn at or near one end of the tube 620, and the other end of each sleeve 620 is free to move relative to the tube 610.

In some embodiments, the user can optionally insert at least one removably insertable rib 622 in at least a respective one of the plurality of sleeves 620. In some embodiments, the ribs are inserted after pulling the helical yarns or fibers 630 to cinch the tube 610. The at least one rib 622 is formed of a material that is more rigid than a material of the tubular woven mesh. The rib can comprise any of a variety of materials, such as wood, plastic or a more rigid material.

Figure 15:
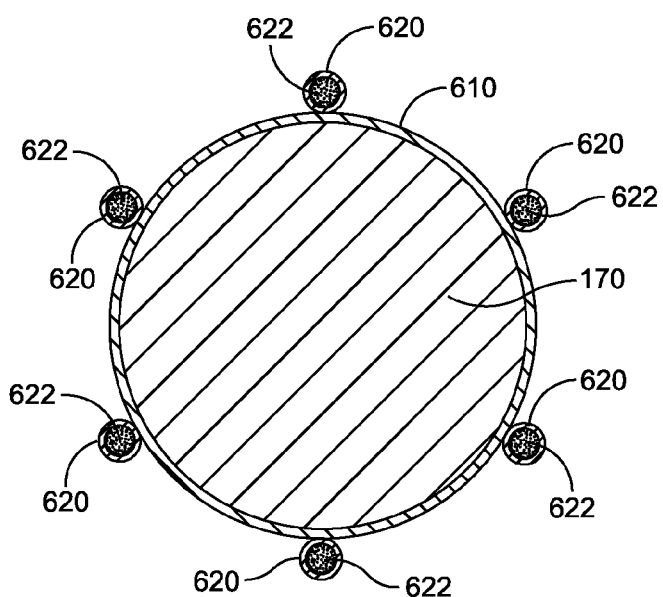
FIG. 15 is a cross sectional view, taken along the lines 15-15, in FIG. 14.

FIG. 15 shows the device 600 after the user inserts six ribs 622 in the respective sleeves 620. The physician can determine on an individual basis how many ribs to insert, if any, and where to put the ribs to achieve desired rigidity in a directional manner. Thus, the physician can select placements of the ribs to increase rigidity in the lateral-medial direction, or in the superior-ventral direction.

Figure 15A:
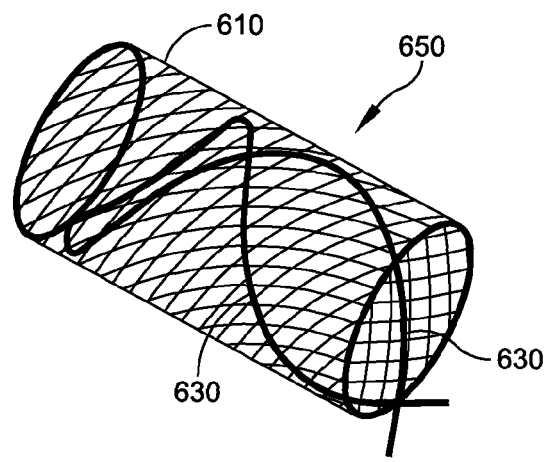
FIG. 15A is a perspective view of an alternative embodiment of external fixation/correction device including helical yarn or fiber that are woven into a tubular mesh.
Figure 15B:
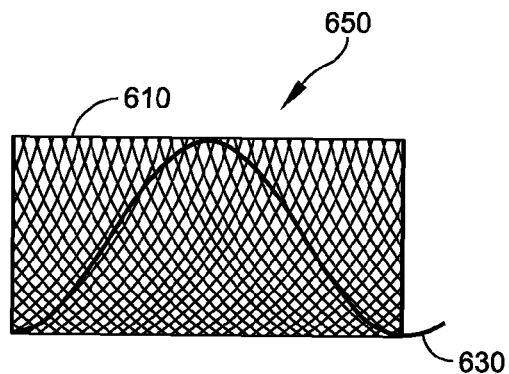
FIG. 15B is a side elevational view of the external fixation/correction device shown in FIG. 15A.
Figure 15C:
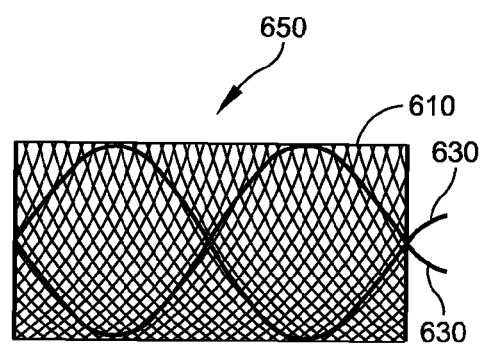
FIG. 15C is a side elevational view of the external fixation/correction device shown in FIGS. 15A and 15B.
Figure 16:
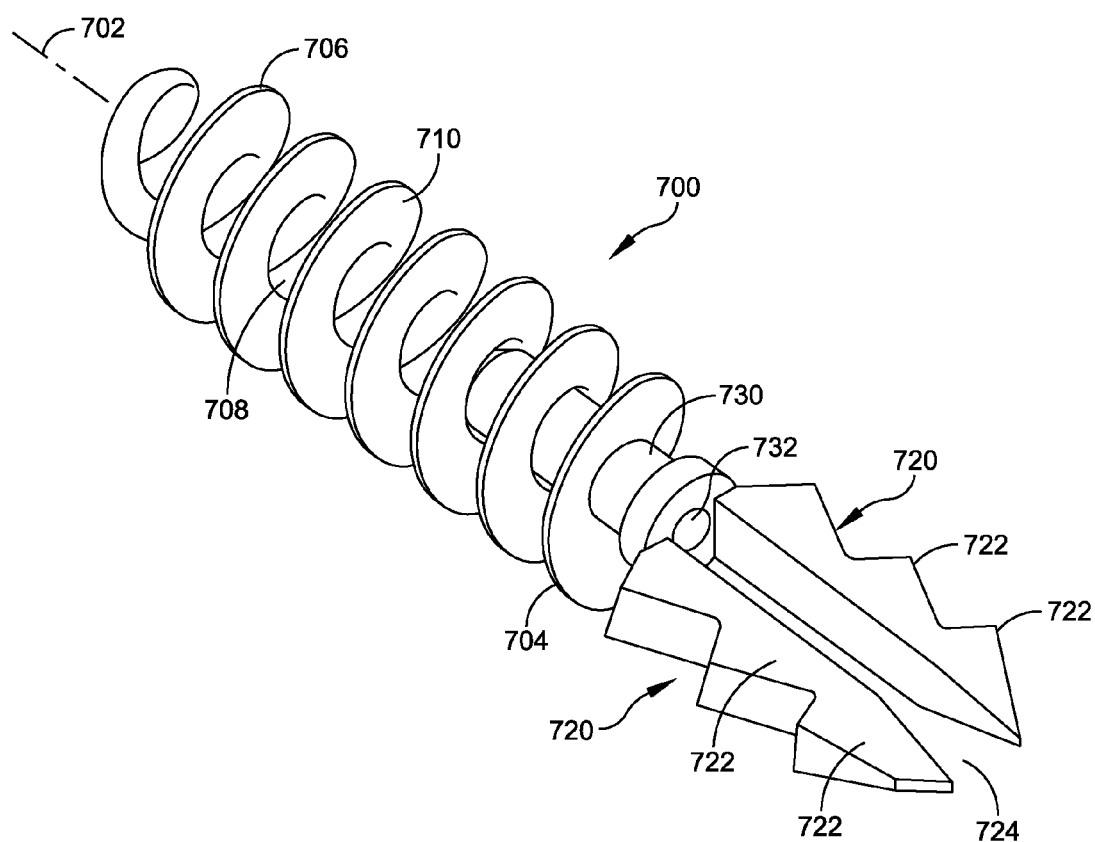
FIG. 16 is a perspective view of a bone implant, formed in accordance with the invention used for correcting deformities of a toe or a finger.

FIGS. 12-15 show an embodiment of device 600 having both the helical yarns or fibers 630 and the sleeves 620. In other embodiments, the device includes a tube 610 with the sleeves 620, but without the helical yarns or fibers 630. In other embodiments, as shown in FIGS. 15A-15C, the device 650 includes a tube 610 with the helical yarns or fibers 630, but without the sleeves 620. When cinched, the helical yarns or fibers 630 causes a bent joint of digit 170 to straighten through the application of a compressive force along the helix.

Although FIGS. 12-15C show the device 600 used alone, the device 600 can be used in combination with any of the devices shown in FIGS. 1-11. In particular, in some embodiments, the device 300 (FIG. 5) or 400 (FIGS. 6-11) can be applied over the device 600. The physician applies device 600 and cinches the helical yarns or fibers 630, and optionally inserts one or more ribs 622 in sleeves 620. Then the physician places the device 300 or 400 over the digit and tightens the clamps 312 or 112 at each end of the device 300 or 400. The physician attaches the drill guide 500 and performs the drilling (e.g., for K-wire insertion). This is just one example, and the device 600 can be used with other external fixation devices to provide compression and support during surgical procedures.

FIGS. 16-19 show an embodiment of a bone implant 700 suitable for correcting a deformity such as a hammertoe. This device 700 addresses the common secondary procedure stabilize the metatarsophalangeal (MTP) joint by releasing the joint capsule and employing a temporary fixation wire. The bone implant 700 comprises a helical threaded member 710 having first and second ends 704, 706 and a longitudinal central opening 708 extending from the first end 704 to the second end 706. The longitudinal central opening has a longitudinal axis 702.

At least one blade 720 integrally attached to the first end 704 of the helical threaded member 710. The blade 720 extends in a radial direction away from the longitudinal axis 702. The blade 720 has an outer edge with a plurality of teeth thereon 722. The blade 720 has an outer edge with a plurality of teeth thereon 722. In some embodiments, as shown in FIGS. 16-19, the implant 700 has two blades evenly spaced and symmetrically arranged to extend in opposite radial directions away from the longitudinal axis 702. A central tube 730 with a central cannula 732 runs along the central axis for a portion of the length of the helical threaded member.

In some embodiments, as shown in FIGS. 16-19, the helical threaded member 710 has a cork-screw shape. The central longitudinal opening (referred to herein as a cannula) of the helical threaded member 710 is open to the exterior of the device. The central opening 708 is continuous with the cannula 732 of the central tube 730 and the cannula 724 which extends to the end of blades 720. This configuration is analogous to a cannula diameter greater than the minor diameter of a screw. The cork screw configuration allows implantation over a k-wire, which is used to address metatarsophalangeal (MTP) joint soft-tissue contracture. The cork-screw configuration of helical threaded member 710 allows both axial compression (FIG. 17) and extension (FIG. 18) and perpendicular bending flexion (FIG. 19), similar to the range of motion of a coiled spring. This provides additional flexibility in the joint as well as enhanced bone integration within the threads of the helical threaded member 710. The degree of flexibility is a function of material properties and geometry and can be controlled and optimized.

Figure 17:
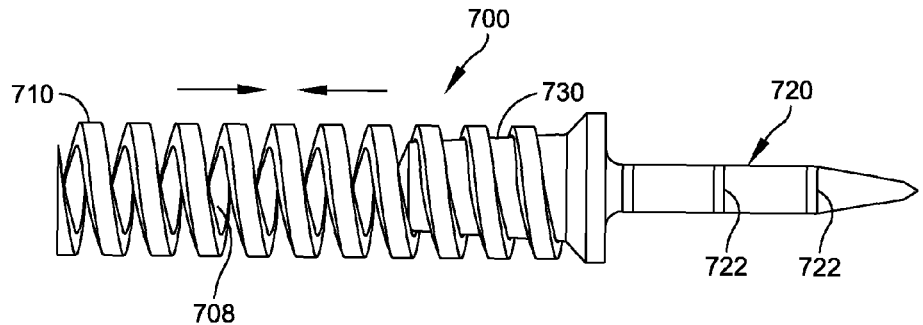
FIG. 17 is a side elevational view of the bone implant shown in FIG. 16.
Figure 18:
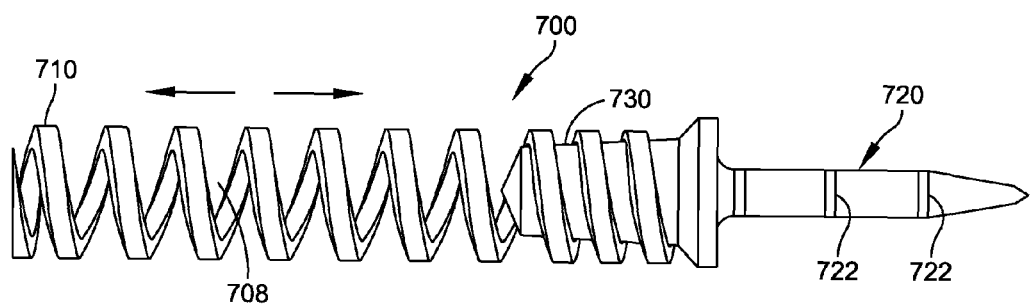
FIG. 18 is a further side perspective view of the bone implant shown in FIGS. 16 and 17.
Figure 19:
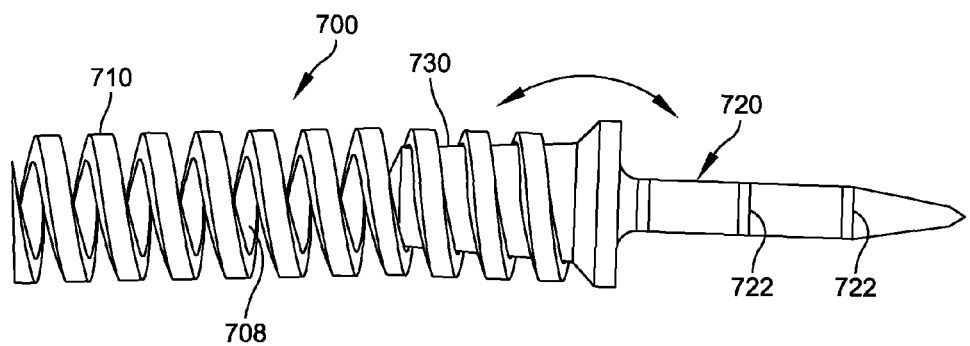
FIG. 19 is a side elevational view of the bone implant shown in FIG. 18, showing the compliance of a helical threaded member.

In some embodiments, implant 700 comprises a material having super-elastic material properties, such as nitinol. In other embodiments, the material is selected to include shape memory properties. Shape memory alloys, such as Nickel Titanium (nitinol), undergo a phase transformation in their crystal structure when cooled from the stronger, high temperature form (Austenite) to the weaker, low temperature form (Martensite). When heated after deformation, the shape memory material recovers its original shape. For example, an implant 700 formed of a material with shape memory is set in the expanded state (FIG. 18), and implanted. Then the device 700 compresses when introduced into the body due to temperature increase (FIG. 17). This ensures compression at the joint while maintaining some flexibility. Also, nitinol exhibits superelasticity if deformed in an environment above their transformation temperatures and will change phase from austenite to stress-induced martensite, allowing it to be strained from ~2-6% with nearly constant stress & return from martensite to austenite during unloading.

In the configuration as shown, the cantilevered blades 720 deflect inwards when radial force is applied, allowing compatibility with an undersized preparation hole. When inserted in the bone, the cantilever blades 720 flex outward increasing fixation in the bone. The outward spring force of the blades 720 is a function of the material properties and geometry, and can be controlled and optimized.

Figure 20:
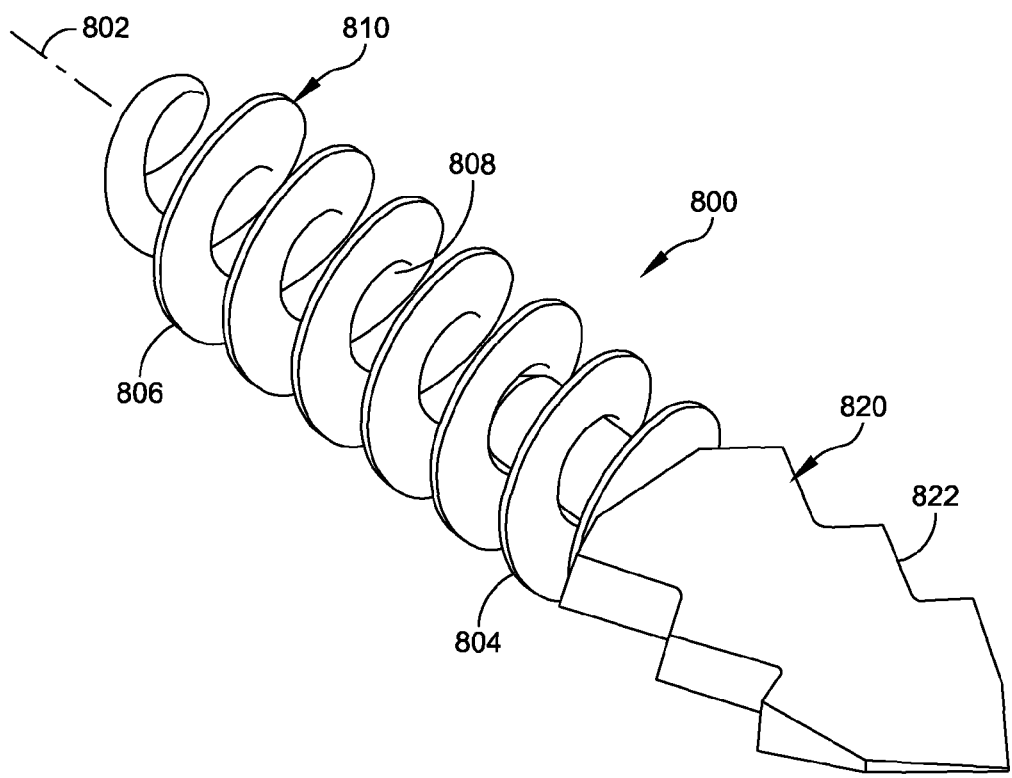
FIG. 20 is a perspective view of an alternative embodiment of bone implant formed in accordance with the invention.

FIG. 20 shows an embodiment of a device 800 which is similar to the device 700 of FIGS. 16-19, except that a single blade 820 with teeth 822 is provided. The bone implant 800 comprises a helical threaded member 810 having first and second ends 804, 806 and a longitudinal central opening 808 extending from the first end 804 to the second end 806. Device 800 is partially cannulated, providing greater flexibility along the helical threaded member 810, along the axis 802 from the first end 804 to the second end 806. Compared to the device 700, the single blade configuration of blade 820 provides greater rigidity when inserted in the bone. In some embodiments, the device 800 comprises a superelastic, shape memory alloy, such as nitinol, providing the expansion/contraction properties of the device 700, but with greater rigidity.

Figure 21:
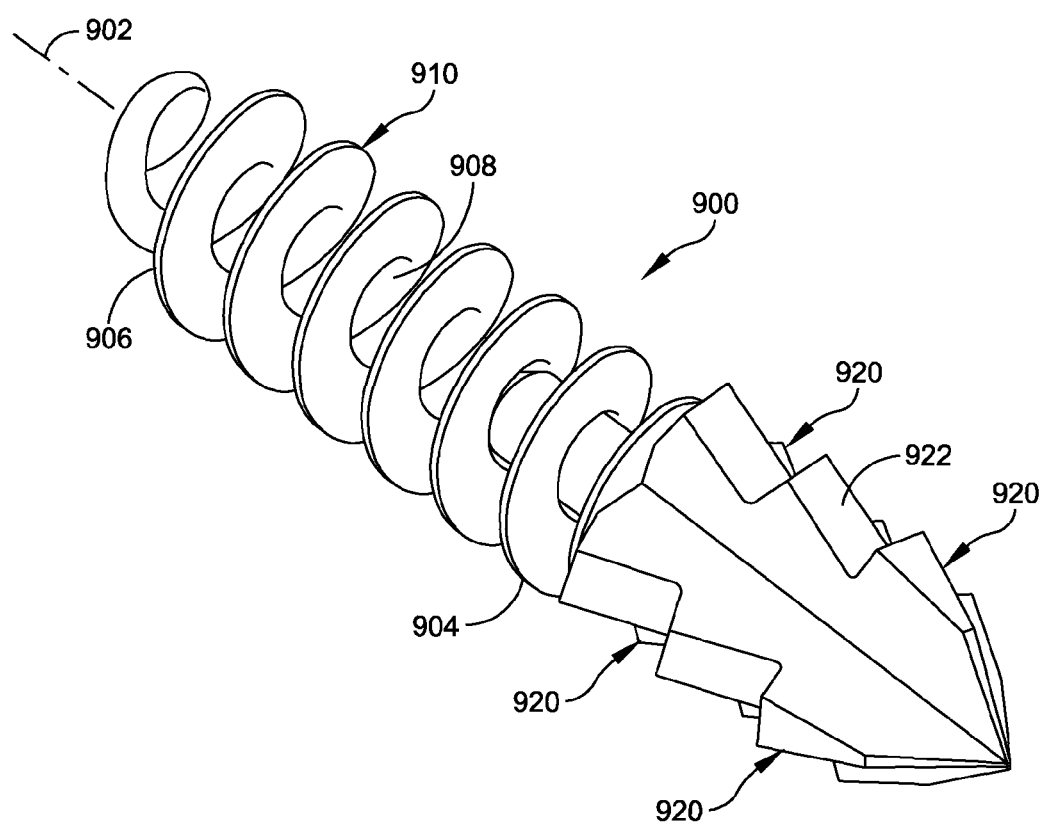
FIG. 21 is a perspective view of yet another embodiment of bone implant, including a multiple barbed end.
Figure 22:
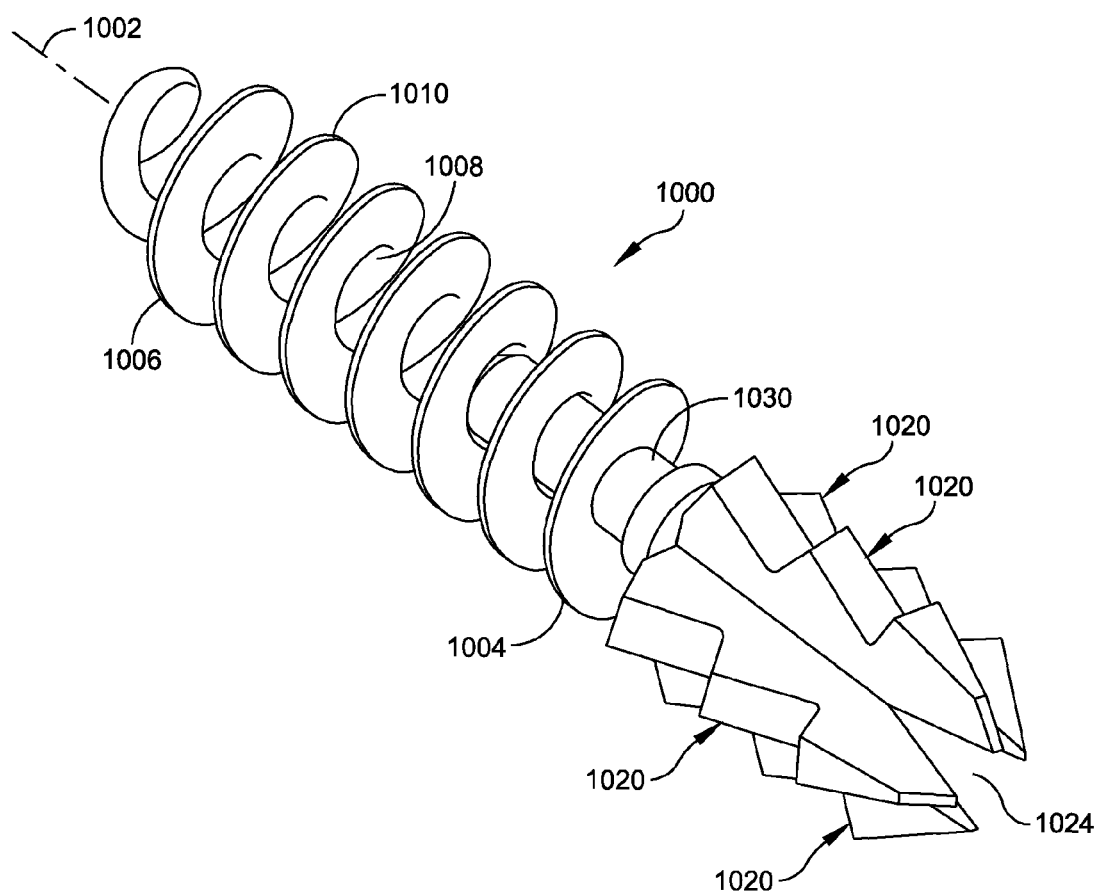
FIG. 22 is a perspective view of a further embodiment of bone implant formed in accordance with the invention, including an alternative multiple barb portion.

FIG. 21 shows an embodiment of a partially cannulated device 900 which is similar to the device 800 of FIG. 20, except that four perpendicular blades 920 with teeth 922 are provided in a continuous, cross-blade configuration. The bone implant 900 comprises a helical threaded member 910 having first and second ends 904, 906 and a longitudinal central opening 908 extending from the first end 904 to the second end 906. Compared to the devices 700 and 800, the cross-blade configuration of blades 920 provides greater rigidity when inserted in the bone. The cross-blade configuration can provide a greater degree of fixation. The cross-blade configuration allows implant pre-drill (circular) preparation instead of broaching. Using an undersized pre-drill step, the crossed blades 920 achieve fixation by circumferential interference with the surrounding bone. In some embodiments, the device 900 comprises a superelastic shape memory alloy, such as nitinol, providing the expansion/contraction properties of the device 700 described above but with greater rigidity & fixation FIG. 22 shows an embodiment of a fully cannulated device 1000 which is similar to the device 700 of FIGS. 16-20, except that four perpendicular blades 1020 are provided in a cross-blade configuration, evenly spaced around the longitudinal axis. The central opening 1008 is continuous with the cannula (not shown in FIG. 22) of the central tube 1030 and the cannula 1024 which extends to the end of blades 1020. A K-wire or the like can be placed through the central opening 1008 of helical threaded member 1010, along the axis 1002 from the first end 1004 to the second end 1006. Compared to the device 700, the four blade configuration of blades 1020 can provide a greater degree of fixation. The cross-blade configuration allows implant pre-drill (circular) preparation instead of broaching. Using an undersized pre-drill step, the crossed blades 1020 achieve fixation by circumferential interference with the surrounding bone. In the configuration of FIG. 22, the four cantilevered blades 1020 deflect inwards when radial force is applied, allowing compatibility with an undersized preparation hole. When inserted in the bone, the cantilever blades 1020 flex outward increasing fixation in the bone. The outward spring force of the blades 1020 is a function of the material properties and geometry, and can be controlled and optimized. In some embodiments, the device 1000 comprises a superelastic, shape memory alloy, such as nitinol.

Figure 23:
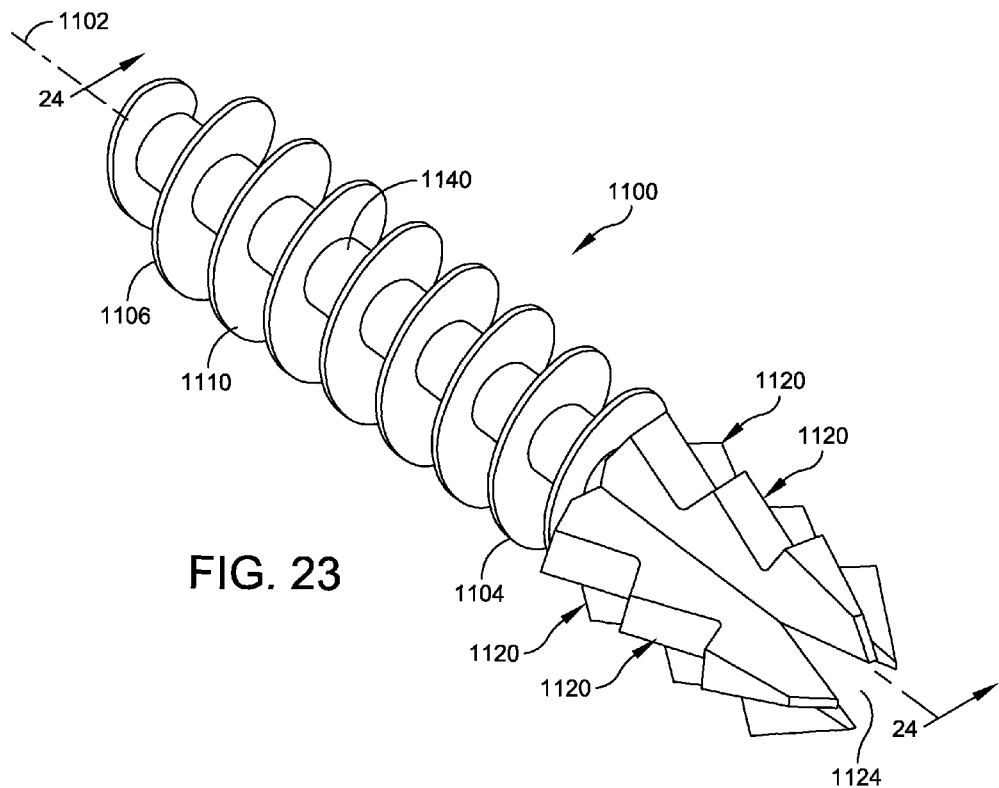
FIG. 23 is a perspective view of the bone implant shown in FIG. 22.
Figure 24:
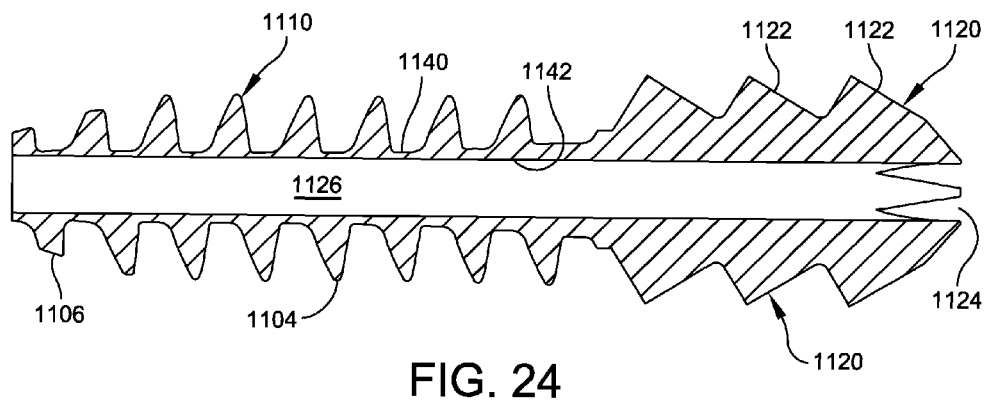
FIG. 24 is a cross sectional view of the bone implant shown in FIG. 23 is taken along lines 24-24.
Figure 25:
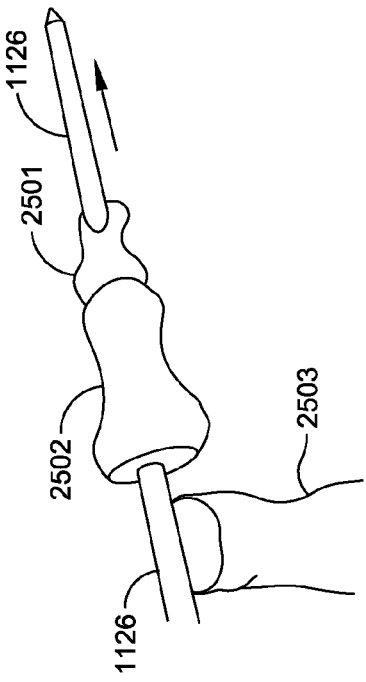
FIG. 25 is a perspective view of a proximal bone that has been pre-drilled to receive a K wire in accordance with one method of the invention.

FIGS. 23 and 24 show an embodiment of a fully cannulated implant 1100 which is similar to the device 1000 of FIG. 22, except that the helical threaded member 1110 of implant 1100 has a minor diameter larger than a diameter of the longitudinal central opening 1124, so that the helical threaded member 1110 has a central tube 1140 with a continuous inner surface 1142 around the longitudinal central opening (cannula) 1124. In implant 1100, four perpendicular blades 1120 with teeth 1122 are provided in a cross-blade configuration, evenly spaced around the longitudinal axis 1102. In other embodiments, only two cantilever blades (similar to blades 720 in FIG. 16) are provided, but the rest of the implant 1100 is otherwise the same. In some embodiments, the device 1000 comprises a superelastic, shape memory alloy, such as nitinol.

A K-wire or the like can be placed through the central opening 1124 of helical threaded member 1110, along the axis 1102 from the first end 1104 to the second end 1106. Compared to the device 700, the four blade configuration of blades 1120 can provide a greater degree of fixation. The cross-blade configuration allows implant pre-drill (circular) preparation instead of broaching. Using an undersized pre-drill step, the crossed blades 1120 achieve fixation by circumferential interference with the surrounding bone.

FIGS. 25-29 show a method for installing the implant 1100. The same sequence of steps is performed for any of the fully cannulated implants, such as implant 700 (FIG. 16), and implant 1000 (FIG. 22). Note that in the views of FIGS. 25-27, the proximal direction is left and the distal direction is right, but in the views of FIGS. 28 and 29, the proximal direction is right and the distal direction is left In FIG. 25, the proximal bone (phalanx) 2503 is pre-drilled to receive the K-wire 1126, and the physician broaches the middle phalanx 2502.

Figure 26:
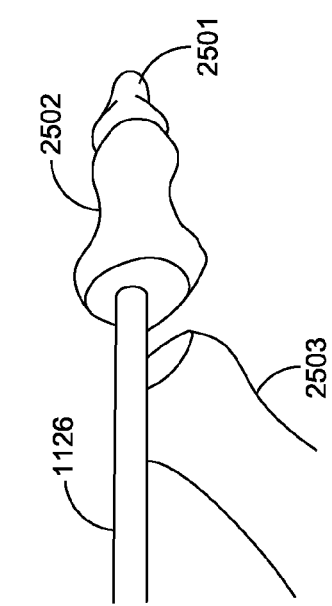
FIG. 26 is a perspective view of a proximal bone shown in FIG. 25 illustrating a physician drilling distally through a middle phalanx.
Figure 27:
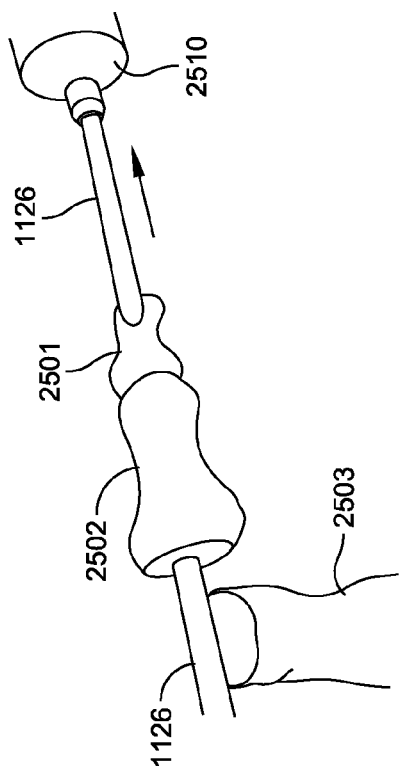
FIG. 27 is a perspective view showing a K wire exposed with a drill attached to the distal end of the K wire.

Then, the physician drills distally through middle phalanx 2502 and through the tip of the toe 2501 with the K-wire 1126, as shown in FIG. 26.

Once the K-wire is exposed, a drill 2510 (shown in FIG. 27) is attached to the distal end of the K-wire 1126. The K-wire 1126 is backed out towards the distal end of the bone 2501, until the proximal tip of the K-wire 1126 is sub-flush with the joint line (i.e., withdrawn past the proximal end of middle phalanx 2502. In some embodiments, the K-wire is drawn past the end of the middle phalanx 2502 by a distance greater than a length of the blades 1120.)

Figure 28:
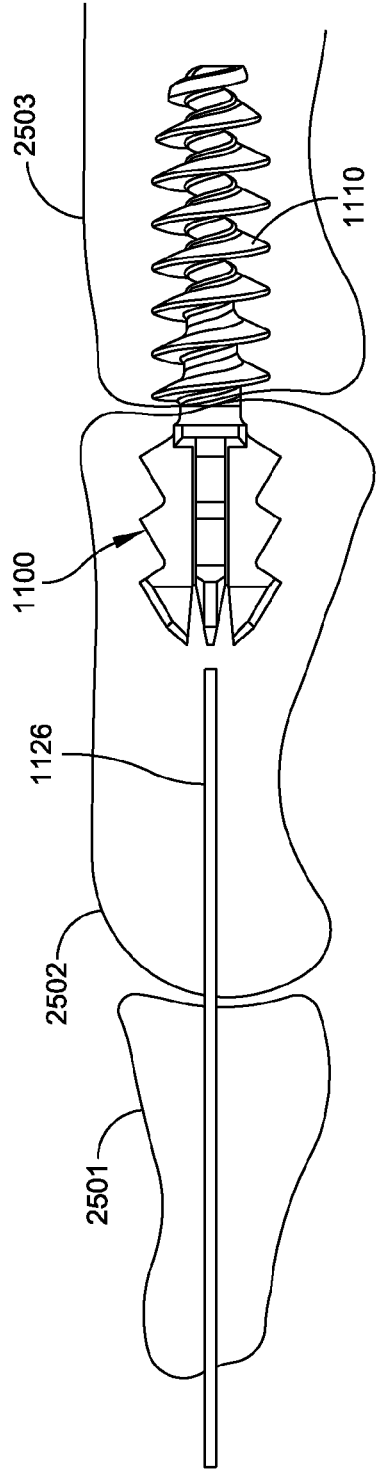
FIG. 28 is a side elevational view, partially in perspective, of a proximal phalanx having a helical threaded portion of a bone implant fully seated.
Figure 29:
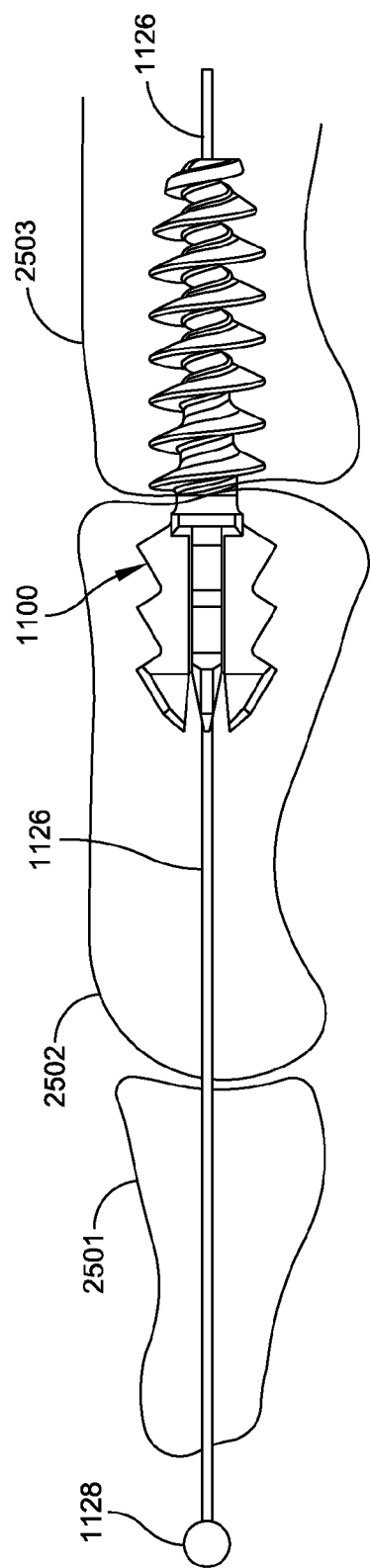
FIG. 29 is a perspective view, similar to FIG. 28, showing K wire fully seated within the bone implant and proximal phalanx.
Figure 30:
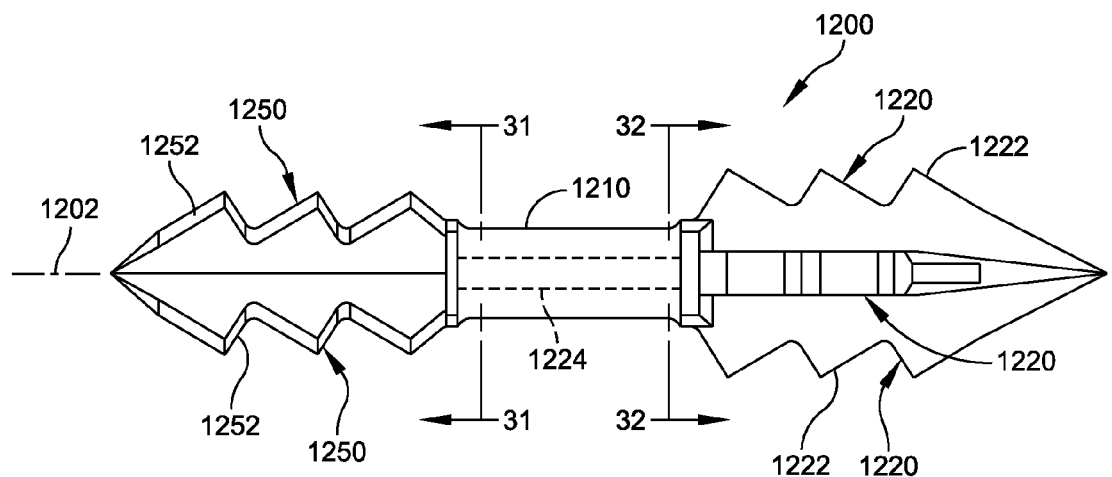
FIG. 30 is a side elevational view of a bone implant in accordance with a further embodiment of the invention.

The helical threaded portion 1110 of the implant 1100 is then advanced into the proximal phalanx 2503 until the implant 1100 is fully seated. Once the implant 1100 is fully seated, the physician closes the joint, forcing the blades 1120 into the previously broached canal as shown in FIG. 28.

With a correctly aligned joint (optionally using one of the external fixation devices shown in FIGS. 1-15), the physician advances the K-wire 1126 in the proximal direction, through the cannulated implant 1100 into the MP joint. They physician caps the K-wire 1126 with a Jurgan ball 1128, completing the installation.

FIGS. 30-34 show a bone implant 1200 comprising a central shaft 1210 having first and second ends and a longitudinal axis. A first set of blades 1220 are integrally attached to the first end of the central shaft 1210. The first set of blades 1220 extends in a radial direction away from the central shaft 1210. Each of the first set of blades 1220 has an outer edge with a plurality of teeth 1222 thereon.

A second set of blades 1250 with teeth 1252 are integrally attached to the second end of the central shaft 1210. The second set of blades 1250 extend in the radial direction away from the central shaft 1210. Each of the second set of blades 1250 has an outer edge with a plurality of teeth 1222 thereon. The second set of blades are rotationally offset from the first set of blades.

Figure 31:
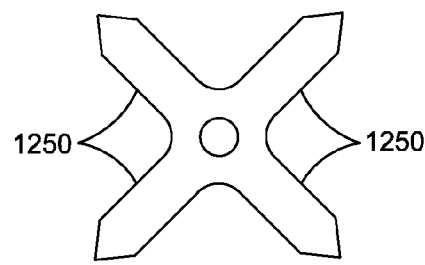
FIG. 31 is an end view of the bone implant shown in FIG. 30.
Figure 32:
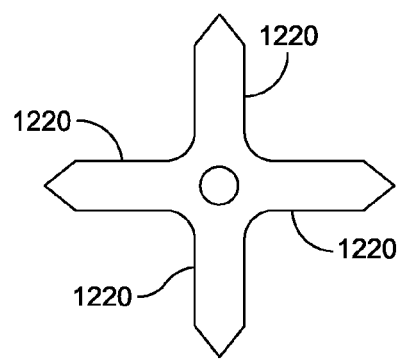
FIG. 32 is a further end view of the bone implant shown in FIG. 30.

In some embodiments, each one of the second set of blades 1250 is rotationally spaced midway between an adjacent pair of the first set of blades 1210. For example, in the implant of FIGS. 30-34, there are four first blades 1220 and four second blades 1250. The angular spacing between each second blade 1250 and the adjacent first blades 1210 on either side is 45 degrees. FIGS. 31 and 32 show the angular offsets between the two sets of blades 1220, 1250.

In some embodiments, the bone implant 1200 has a cannula 1224 extending along the longitudinal axis 1202 from a first end of the bone implant to a second end of the bone implant. In other embodiments, the implant is solid, with no cannula. In some embodiments, the device 1000 comprises a superelastic, shape memory alloy, such as nitinol.

In some embodiments, an instrument is provided that inserts a broach in the bone on one side of the joint in a first orientation, and then is rotated +/−45 degrees to broach the bone on the other side of the joint in a second orientation rotationally offset from the first orientation. The instrument has a shape to match the cross-blade configuration 1220 of the implant 1200. In other embodiments, a K-wire channel is pre-drilled into the bone prior to inserting the implant, and no broach is required. In either case, the physician uses a safety tool to handle the implant 1200. The safety tool has a gripping handle and a head shaped to receive either the blades 1220 or the blades 1250, so the physician is not harmed by the blades 1220, 1250.

The inventors have determined that one of the sources of problems in hammertoe implants is implant loosening after insertion. The rotational offset between blades 1220 and blades 1250 provides a different orientation on the distal end and the proximal end to help prevent against the blades from loosening.

Figure 33:
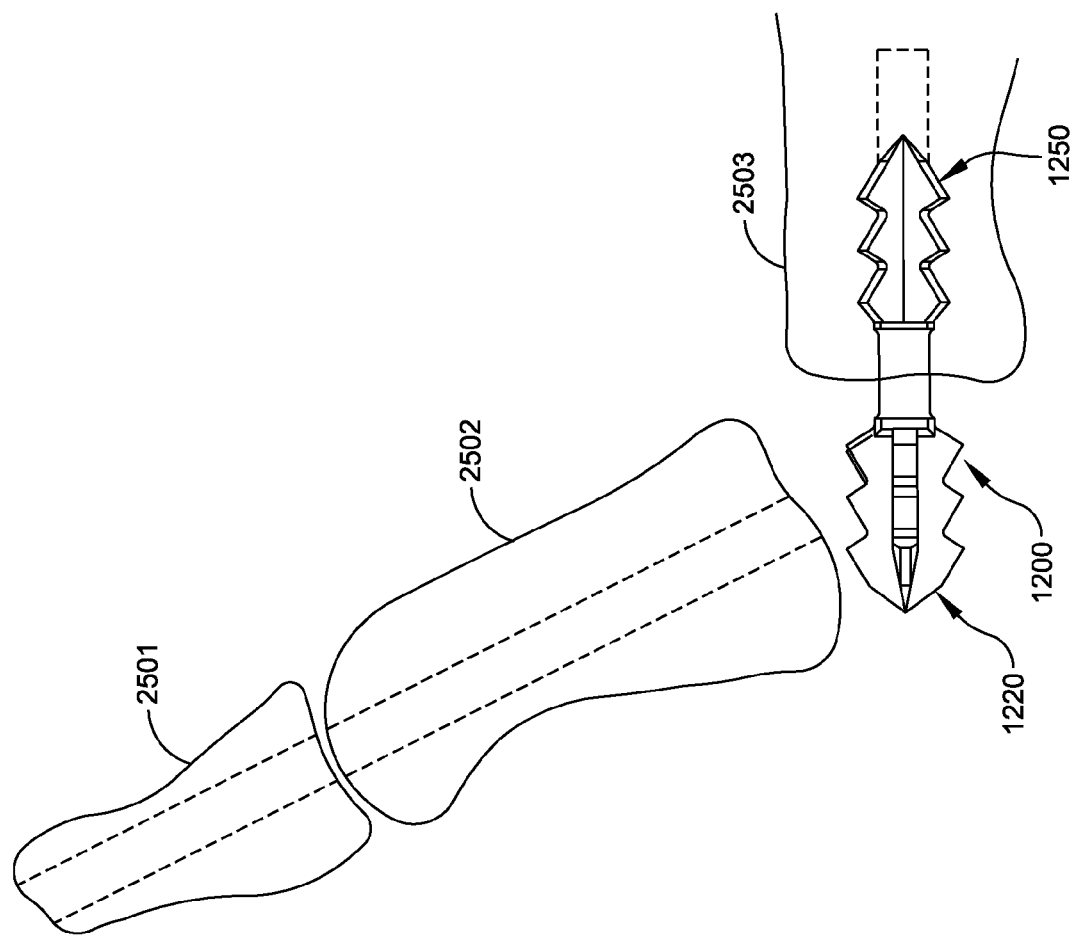
FIG. 33 is an exploded, partially perspective view of a set of phalanges having a bone implant lodged within a portion.
Figure 34:
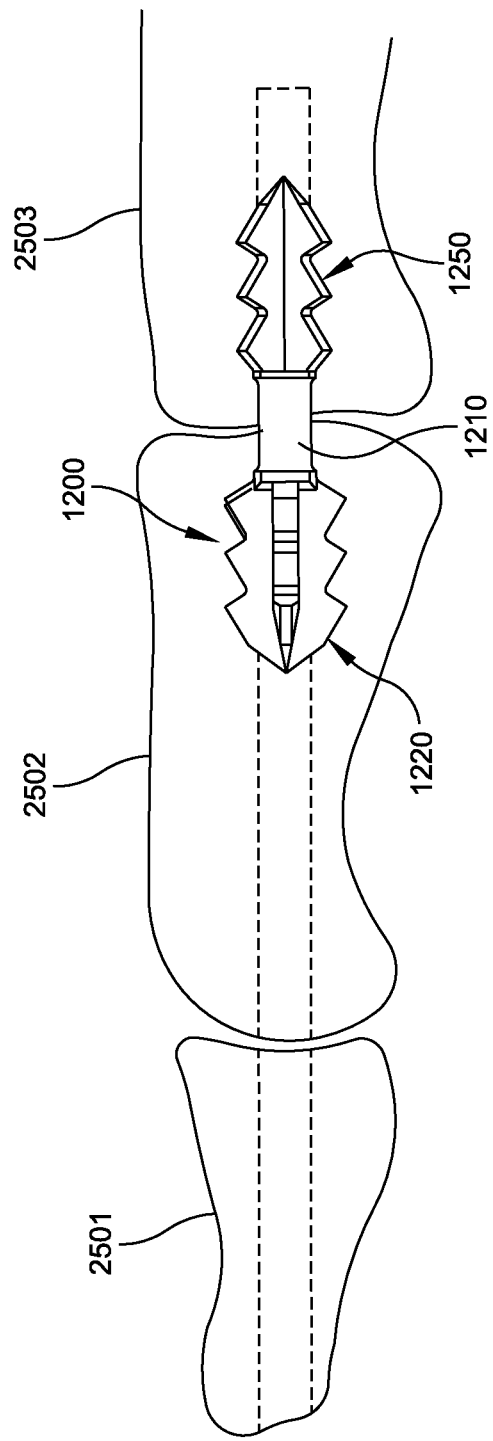
FIG. 34 is a side elevational view, partially in phantom partially in perspective, showing the bone implant of FIG. 33 fully assembled within the proximal and distal phalanges.

FIGS. 33-34 show the method of insertion. First, the bones 2501-2503 are pre-drilled as shown and described above with reference to FIGS. 25-27, and the physician inserts the K-wire 1126 across the joint. The alignment may be checked by fluoroscopy to confirm where to insert the implant. The K-wire 1126 is backed out beyond the proximal end of the middle phalanx 2502.

As shown in FIG. 33, the physician inserts the blades 1220 of implant 1200 in the proximal phalanx 2503, where the K-wire pre-drilled hole is visible. The physician can use the above-mentioned safety tool for this purpose.

Then as shown in FIG. 34, the physician takes the PIP joint and places the broached or pre-drilled side of the middle phalanx 2502 over the blades 1250 and presses the middle phalanx into place, with the implant now embedded in both the middle phalanx 2502 and the proximal phalanx 2503.

If the implant 1200 is cannulated, then the K-wire 1126 is advanced through the implant in the same manner described above with reference to FIG. 29, and a Jurgan ball 1128 is attached.

Although the subject matter has been described in terms of exemplary embodiments, it is not limited thereto. Rather, the appended claims should be construed broadly, to include other variants and embodiments, which may be made by those skilled in the art.

What is claimed is:

1. A bone implant comprising:
    a helical threaded member having first and second ends and a longitudinal central opening extending from the first end to the second end, the longitudinal central opening having a longitudinal axis, wherein the helical threaded member has a central tube with a central cannula running along a central axis for a portion of the length of the helical threaded member; and
    at least one blade integrally attached to the first end of the helical threaded member, the blade extending in a radial direction away from the longitudinal axis, the blade having an outer edge with a plurality of teeth thereon.

2. The bone implant of claim 1, wherein the helical threaded member has a minor diameter larger than a diameter of the longitudinal central opening, so that the helical threaded member has a continuous inner surface around the longitudinal central opening.

3. The bone implant of claim 1, wherein the helical threaded member has a cork-screw shape.

4. The bone implant of claim 1, wherein the at least one blade includes two or four blades evenly spaced around the longitudinal axis and located adjacent to said central tube.

5. The bone implant of claim 1, wherein the longitudinal central opening extends to an end of the at least one blade opposite the helical threaded member.

6. The bone implant of claim 1, wherein the bone implant comprises a shape memory alloy.

7. The bone implant of claim 1, wherein the bone implant comprises a superelastic alloy.

8. The bone implant of claim 1, wherein the bone implant comprises nitinol.

9. A bone implant comprising:
    a helical threaded member having first and second ends and a longitudinal central opening extending from the first end to the second end, the longitudinal central opening having a longitudinal axis, wherein the helical threaded member has a central shaft having first and second ends and a longitudinal axis extending within said longitudinal central opening from said first end; and
    a first set of blades integrally attached to the first end of the central shaft, the first set of blades extending in a radial direction away from the central shaft, each of the first set of blades having an outer edge with a plurality of teeth thereon; and
    a second set of blades integrally attached to the central shaft, the second set of blades extending in the radial direction away from the central shaft, each of the second set of blades having an outer edge with a plurality of teeth thereon, the second set of blades rotationally offset from the first set of blades, the first and second set of blades cantilevered for flexing inward or outward radially.

10. The bone implant of claim 9, wherein each one of the second set of blades is rotationally spaced midway between an adjacent pair of the first set of blades.

11. The bone implant of claim 9, wherein the bone implant has a cannula extending along the longitudinal axis from a first end of the bone implant to a second end of the bone implant.

* * * * *